United States Patent
Park et al.

(10) Patent No.: US 11,327,079 B2
(45) Date of Patent: May 10, 2022

(54) DIRECT DETECTION OF THE ACTIVE FORM OF BETA-LACTAM-HYDROLYSING ENZYMES BY USING MASS SPECTROPHOTOMETRY

(71) Applicant: Diatech Korea Co., Ltd., Seoul (KR)

(72) Inventors: Kye Shin Park, Seoul (KR); Joon Sang Park, Seoul (KR); Eun Hee Lee, Gyeonggi-do (KR); Dong Hwi Hwang, Gyeonggi-do (KR); In Jung Ji, Seoul (KR); Jae Woo Roh, Seoul (KR); Jin Sung Ahn, Seoul (KR); Eun-Jeong Yoon, Seoul (KR); Ji Hye Ko, Gyeonggi-do (KR)

(73) Assignee: DK HOLDINGS COMPANY, LTD, Seoul (KR)

( * ) Notice: Subject to any disclaimer, the term of this patent is extended or adjusted under 35 U.S.C. 154(b) by 0 days.

(21) Appl. No.: 16/627,710

(22) PCT Filed: Dec. 12, 2018

(86) PCT No.: PCT/KR2018/015783
§ 371 (c)(1),
(2) Date: Mar. 31, 2021

(87) PCT Pub. No.: WO2020/027390
PCT Pub. Date: Feb. 6, 2020

(65) Prior Publication Data
US 2021/0318332 A1    Oct. 14, 2021

(30) Foreign Application Priority Data
Aug. 3, 2018 (KR) .......................... 10-2018-0090772

(51) Int. Cl.
*G01N 33/68* (2006.01)
*C12N 9/86* (2006.01)
*C12Q 1/34* (2006.01)
*C12Q 1/04* (2006.01)
*C12Q 1/06* (2006.01)

(52) U.S. Cl.
CPC ........... *G01N 33/6851* (2013.01); *C12N 9/86* (2013.01); *C12Q 1/045* (2013.01); *C12Q 1/06* (2013.01); *C12Q 1/34* (2013.01); *C12Y 305/02006* (2013.01); *G01N 2560/00* (2013.01)

(58) Field of Classification Search
CPC ... C12Q 1/34; C12Q 1/04; C12Q 1/06; C12Q 1/045; C12N 9/86; G01N 2560/00; G01N 27/64; G01N 33/68; G01N 33/6851; C12Y 305/02006
See application file for complete search history.

(56) References Cited

U.S. PATENT DOCUMENTS

2013/0089886 A1    4/2013  Feng et al.
2016/0138068 A1*   5/2016  Hrabak et al. ........... C12Q 1/04

FOREIGN PATENT DOCUMENTS

JP    2013535974 A    9/2013
JP    2014514566 A    6/2014

OTHER PUBLICATIONS

International Search Report issued in connection with PCT Application No. PCT/KR2018/015783 dated Apr. 4, 2019.
Ghebremedhin, B. et al., 'MALDI-TOF MS based carbapenemase detection from culture isolates and from positive blood culture vials', Ann. Clin. Microbiol. Antimicrob., Feb. 2, 2016, vol. 15, No. 5, pp. 1-6.
Hrabak, J. et al., 'Detection of NDM-1, VIM-1, KPC, OXA-48, and OXA-162 Carbapenemases by Matrix-Assisted Laser Desorption Ionization—Time of Flight Mass Spectrometry', Journal of Clinical Microbiology, 2012 [Electronic Publication] May 2, 2012., vol. 50, No. 7, pp. 2441-2443.

* cited by examiner

*Primary Examiner* — Satyendra K Singh
(74) *Attorney, Agent, or Firm* — Steven M. Shape; Dennemeyer & Associates, LLC

(57) ABSTRACT

The present invention relates to a method of directly detecting, using a mass-spectrometry method, whether a microorganism contained in a sample is resistant to antibiotics, and a kit for detection used therewith. More particularly, the present invention relates to a method and kit for directly detecting an antibiotic hydrolase secreted by a microorganism resistant to antibiotics, thereby directly determining whether the microorganism is resistant to antibiotics. According to the present invention, it is possible to very simply and immediately confirm whether a specific strain is resistant to antibiotics in the field. In particular, a complicated pretreatment process such as proteolysis is not performed, and a complicated identification process of calibrating and then combining the obtained results is not performed. Accordingly, it is possible to realize a method of easily confirming whether antibiotic resistance occurs in just a dozen minutes, compared to a conventional technology in which it takes several days to confirm whether antibiotic resistance occurs, and a simple diagnostic kit used therewith.

10 Claims, 25 Drawing Sheets

DIRECT DETECTION OF THE ACTIVE FORM OF BETA-LACTAM-HYDROLYSING ENZYMES BY USING MASS SPECTROPHOTOMETRY

CROSS-REFERENCE TO RELATED APPLICATIONS

This is a 35 U.S.C. 371 National Stage Patent Application of International Application No. PCT/KR2018/015783, filed Dec. 12, 2018, which claims priority to Korean application 10-2018-0090772, filed Aug. 3, 2018, each of which is hereby incorporated by reference in its entirety.

TECHNICAL FIELD

The present invention relates to a method of directly detecting, using a mass-spectrometry method, whether a microorganism contained in a sample is resistant to antibiotics, and a kit for detection used therewith. More particularly, the present invention relates to a method and a kit for directly detecting an antibiotic hydrolase expressed by a microorganism resistant to antibiotics, thereby directly determining whether the microorganism is resistant to antibiotics.

BACKGROUND ART

The discovery of antibiotics/antimicrobials has opened a new chapter in the treatment of infection, but the increase in the use of antibiotics has caused the development and spread of bacteria resistant to antibiotics. The emergence and spread of such antibiotic-resistant strains is a major cause of failure to treat infectious diseases, and prolongs patient hospitalization times, thereby increasing the economic burden on public health. The worldwide problem of these antibiotic-resistant strains is a major issue in various countries and organizations. In 2013, President Obama of the United States declared the issue of antibiotic resistance to be a major issue for the nation to overcome, and additionally, the World Health Organization (WHO) has warned of the seriousness of antibiotic resistance.

Among antibiotics, carbapenem in particular has strong antibacterial activity, and is considered the last bastion to treat multi-resistant gram-negative rods. However, Enterobacteriaceae resistant to carbapenem has been spreading since the late 2000s.

Carbapenem-resistant strains are resistant to most antibiotics, and thus it is very difficult to perform clinical treatment, causing high mortality rates upon infection. Therefore, the resistance of Enterobacteriaceae to carbapenem may be a very serious threat to national health, and early detection and treatment with an appropriate antimicrobial in an early stage of infection is of the utmost importance.

As a conventional technique for determining the antibiotic resistance of such a strain, there are a culture-antimicrobial sensitivity test, a nucleic acid amplification method, and a mass-spectrometry method.

However, in the case of the typical culture-antimicrobial sensitivity test, primary culturing is performed using a patient specimen, and resistance to the antimicrobial is confirmed through the antimicrobial sensitivity test. About one to five days are required to perform primary culture and an additional one or two days are required to perform the antimicrobial sensitivity test. Therefore, the typical culture-antimicrobial sensitivity test is not suitable as a method for detecting resistance in the early stage of infection.

Meanwhile, in the case of the nucleic acid amplification method, an antibiotic hydrolase is capable of being identified within a relatively short time. However, the nucleic acid amplification method is a method capable of confirming only the presence or absence of a limited range of genes, and nucleic acid fragments of the inactivated enzyme are also detected. Accordingly, there is a problem that it is difficult to directly confirm whether antibiotic resistance is actually expressed.

The mass-spectrometry method is to accurately analyze the type and amount of protein by measuring the mass of the protein or peptide, which is a component constituting the protein, and it is possible to accurately analyze specific proteins in a complex biological sample. With this technical capability, various materials are capable of being measured accurately and simultaneously and then used for diagnosis. In particular, a mass-spectrometry method using MALDI-TOF (matrix-assisted laser desorption ionization time-of-flight) is considered to be the most suitable ultra-fast diagnostic mass-spectrometry method because a large number of samples is capable of being quickly measured. However, direct measurement of the target protein using the MALDI-TOF method has a limitation in measuring a limited amount of the target substance due to the low sensitivity. Therefore, there is a strong need for the development of high-sensitive measurement and quantification methods using MALDI-TOF.

The LC/MS/MS method, used for protein analysis, is highly accurate and easy to automate because a single sample is measured, and is suitable for analyzing complex protein bodies that are mixed. However, it is necessary to increase the sensitivity in order to accurately analyze the concentration of a specific protein, and it is necessary to reduce the time required for measuring one sample in order to analyze a large number of samples.

In view of the cost of diagnosis, the mass spectrometer that is currently used is expensive equipment, and thus is capable of being owned and operated only by a large hospital or a specialized institution that is capable of purchasing and maintaining large equipment. Further, the operation of the instrument requires skilled technicians, and the instrument must be constantly maintained. Accordingly, maintenance and operation of the instrument are costly. Therefore, in order to universally and easily use the mass-spectrometry method for the purpose of diagnosis, it is necessary to develop a simple low-priced instrument that anyone can easily access.

DISCLOSURE

Technical Problem

The present invention has been made considering the problems occurred in the prior art. An object of the present invention relates to a method of directly detecting an antibiotic-decomposing enzyme using a mass-spectrometry method, which is capable of being used immediately in the field, and a simple diagnostic kit used therewith.

Technical Solution

In order to accomplish the above object of the present invention, it includes culturing a strain using a sample collected from a patient, performing pretreatment for mass spectrometry on bacteria strains cultured, and performing the mass spectrometry on pretreated samples using a MALDI-TOF mass spectrometer. The data obtained through performing the mass spectrometry is analyzed, thus determining antibiotic resistance.

In a preferred aspect, the antibiotic is a beta-lactam antibiotic. The antibiotic hydrolase (β-lactamase) to be measured is KPC, NDM, or OXA.

An antibiotic-resistant strain is selected from *Escherichia coli, Klebsiella pneumoniae, Pseudomonas aeruginosa, Acinetobacter baumannii, Bacillus species, Stenotrophomonas maltophilia, Aeromonas species, Bacteroides fragilis, Pseudomonas otitidis, Citrobacter koseri, Enterobacter cloacae*, and more. Preferably, among the Enterobacteriaceae, gram-negative bacteria are used as a target.

In a preferred aspect of the present invention, a protease is not used during the pretreatment of the target sample.

In a preferred embodiment of the present invention, the performing the pretreatment further includes lysing the sample using a lysis buffer including a detergent. The lysing may be directly performed on a plate of a mass spectrometer.

According to another preferred embodiment, performing the pretreatment includes homogenizing the cultured bacteria in a solution including a buffer and sonicating the homogenized sample at room temperature.

According to another preferred embodiment, during the pretreatment, a protease inhibitor may be added.

According to another preferred embodiment, the beta-lactam antibiotic hydrolase is a carbapenemase.

According to another preferred embodiment, the carbapenemase has a genotype of KPC, NDM, or OXA.

According to another preferred embodiment, when a peak appears around m/z of 28,670 to 28,770, active KPC is determined to be present.

According to another preferred embodiment, when a peak appears around m/z of 28,100 to 28,200, active OXA is determined to be present.

According to another preferred embodiment, the detergent is a non-ionic detergent. More preferably, the detergent is selected from the group consisting of OG (n-octyl-β-D-glucopyranoside), OTG (n-octyl-β-D-thioglucopyranoside), DDM (n-dodecyl-β-D-maltopyranoside), OGNG (octyl glucose neopentyl glycol), and DDTM (n-dodecyl-β-D-thiomaltopyranoside).

Meanwhile, the present invention provides a kit for directly detecting an active form of a beta-lactam antibiotic hydrolase using a mass-spectrometry method, and the kit is used for the specific method of the present invention.

According to a preferred embodiment, the kit includes a buffer, a matrix for a MALDI-TOF mass spectrometer, a first standard material, and a second standard material. The first standard material includes a hydrolase to be measured, and the second standard material includes a material for instrument calibration. The lysis buffer may include the detergent of the present invention.

According to another preferred embodiment, the hydrolase is a carbapenemase.

According to another preferred embodiment, the carbapenemase has a genotype of KPC, NDM, or OXA.

Advantageous Effects

According to the present invention, it is possible to very rapidly and simply confirm whether a specific strain is resistant to antibiotics, especially beta-lactam antibiotics. In particular, a complicated pretreatment process such as proteolysis is not performed, and a complicated identification process of calibrating and then combining the obtained results is not performed. Accordingly, it is possible to realize a method of easily confirming whether antibiotic resistance occurs in just a dozen minutes, compared to a conventional technology which takes several days to confirm whether antibiotic resistance occurs, and provide a simple diagnostic kit used therewith.

DESCRIPTION OF DRAWINGS

FIG. 4a shows control data of an *E. coli* TOP10 strain, FIG. 4b shows data of vector pUC18 inserted TOP10 for gene to be added, FIG. 4c shows data of the TOP10 strain expressing OXA-48 via vector pUC18, and FIG. 4d shows data of the TOP10 strain expressing NDM via vector pUC18;

FIG. 8a shows data of a transformed KPN (*Klebsiella pneumoniae*) AK75-pUC18 strain which was inserted with vector pUC18 for gene to be added, and FIG. 8b shows data of a KPN AK75-pUC18-KPC-2 strain expressing KPC-2.

BEST MODE

Figure 1A:
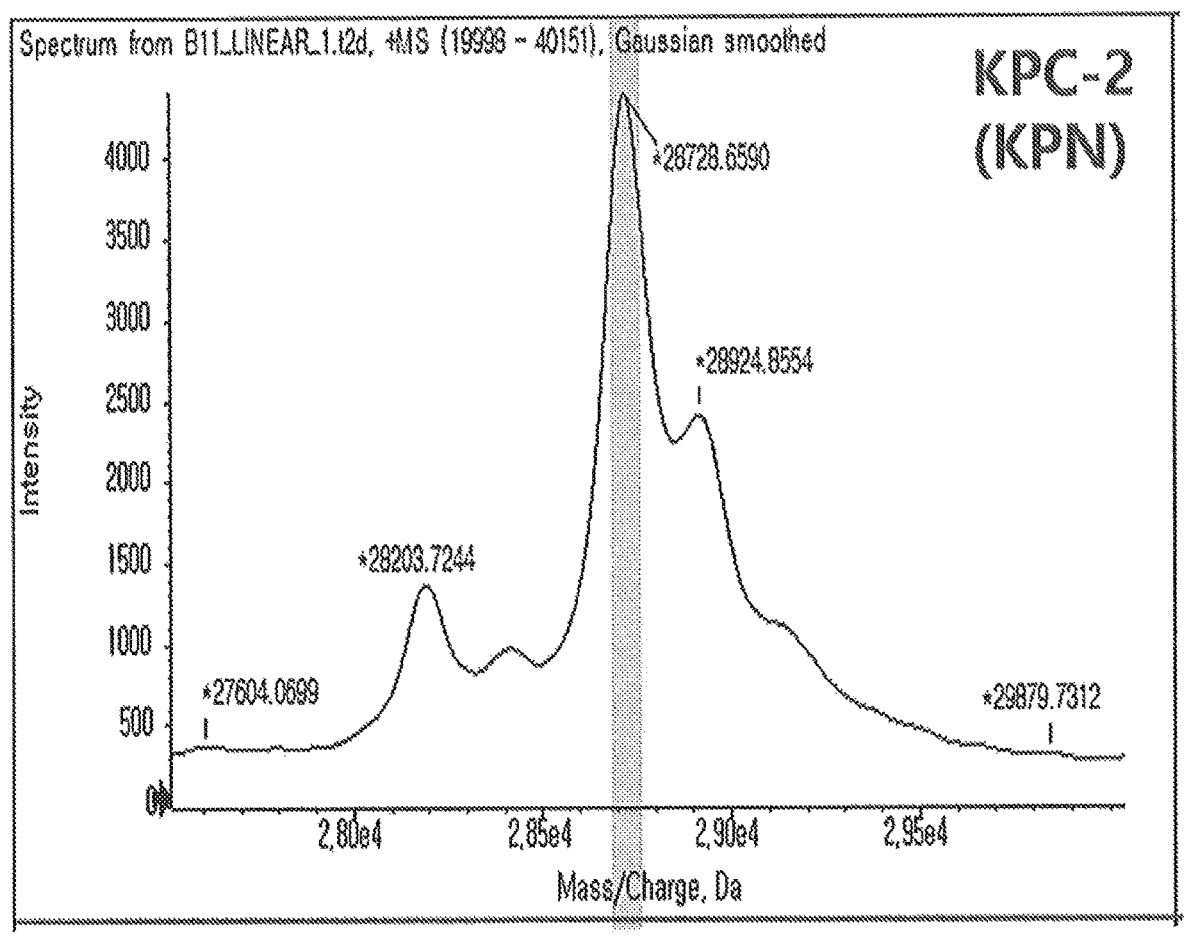
FIG. 1 shows data obtained by identifying carbapenemase-KPC-producing Enterobacteriaceae using MALDI-TOF according to the method of the present invention using a detergent.
Figure 1B:
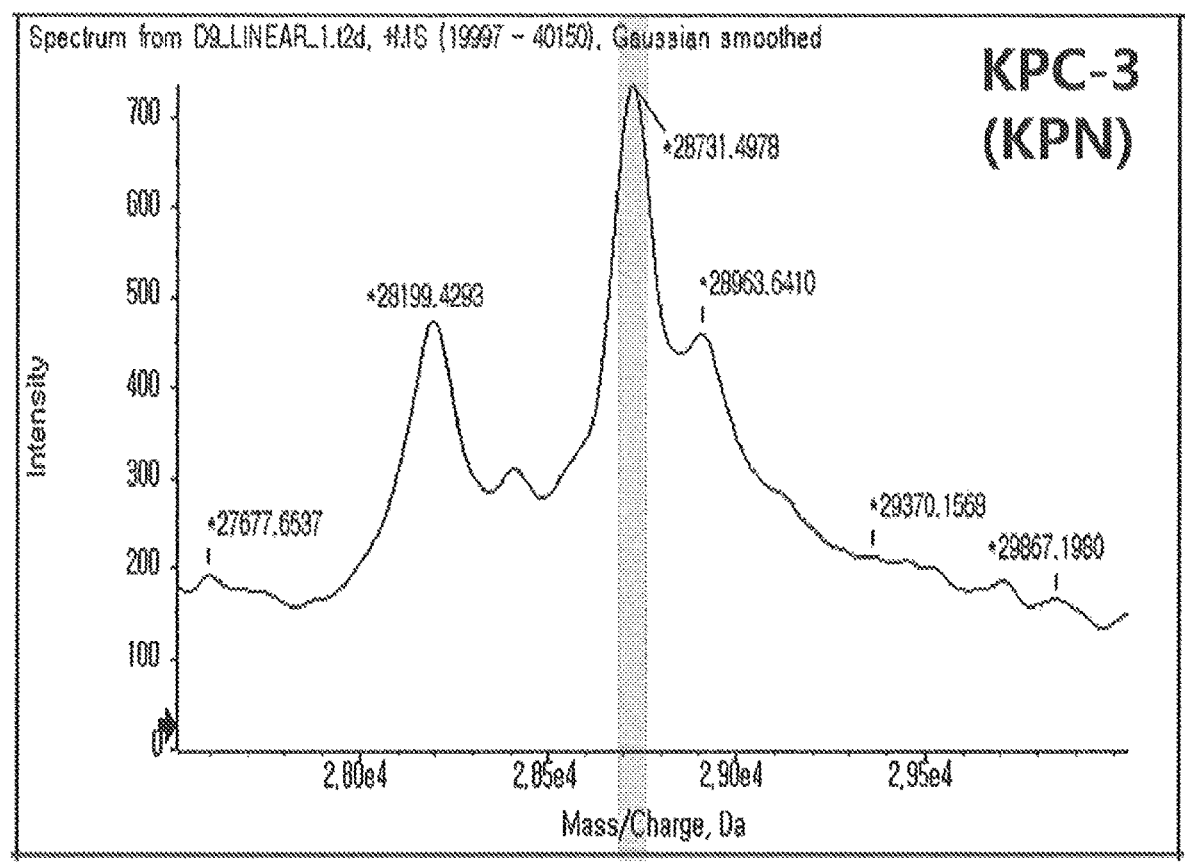
Figure 1C:
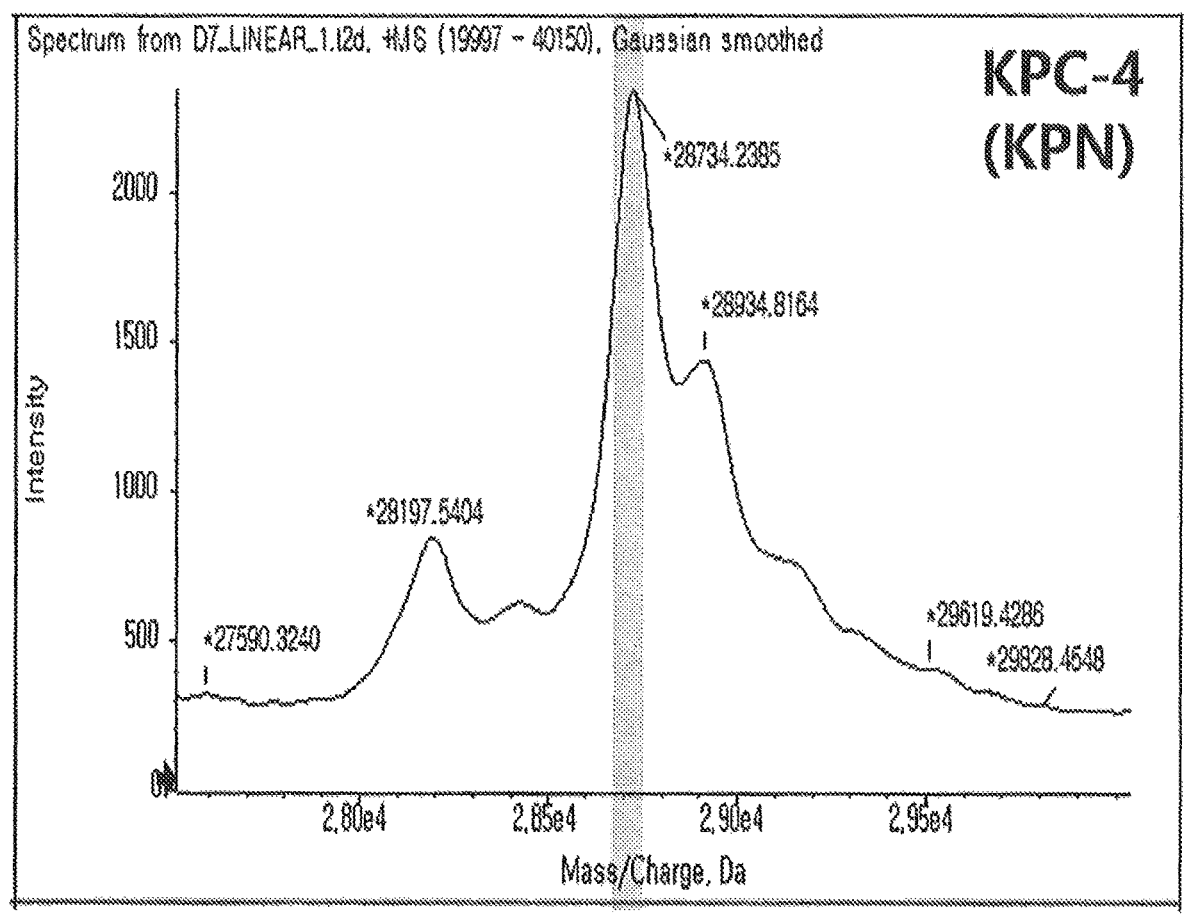
Figure 1D:
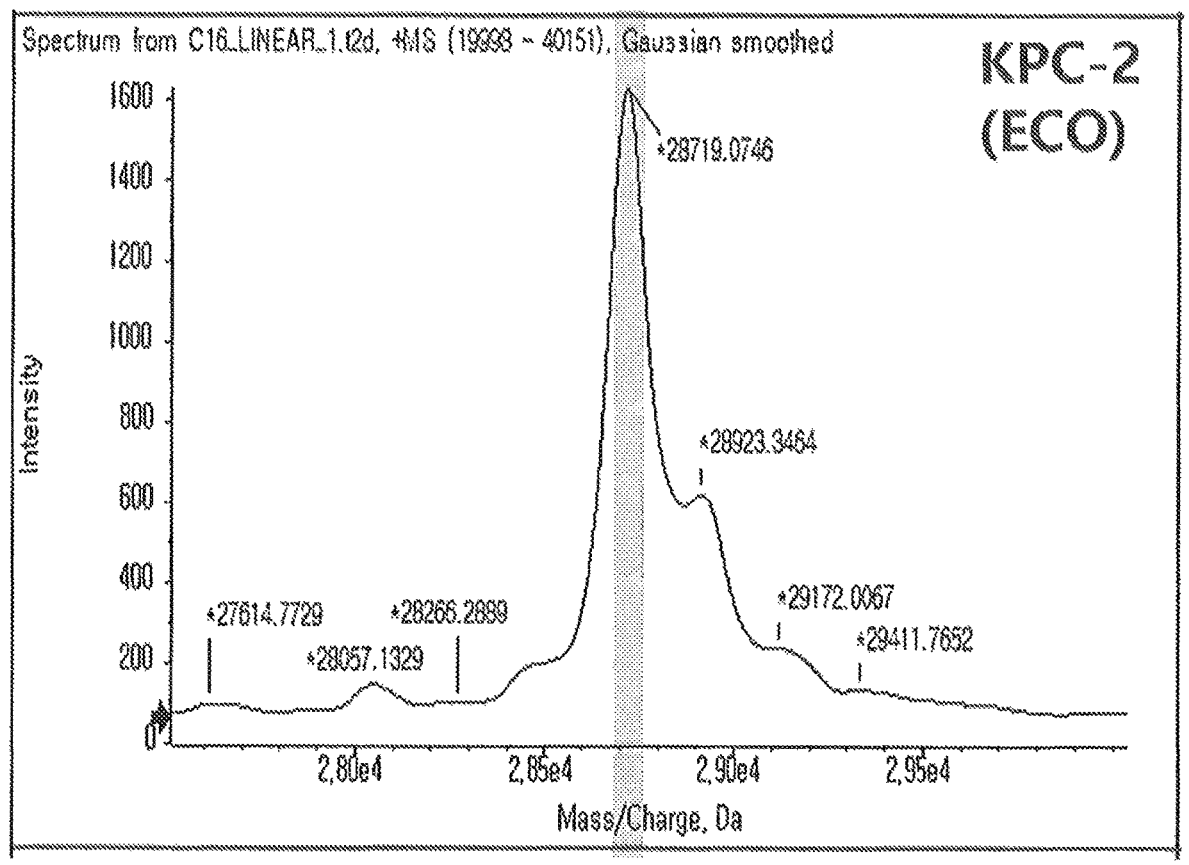
Figure 1E:
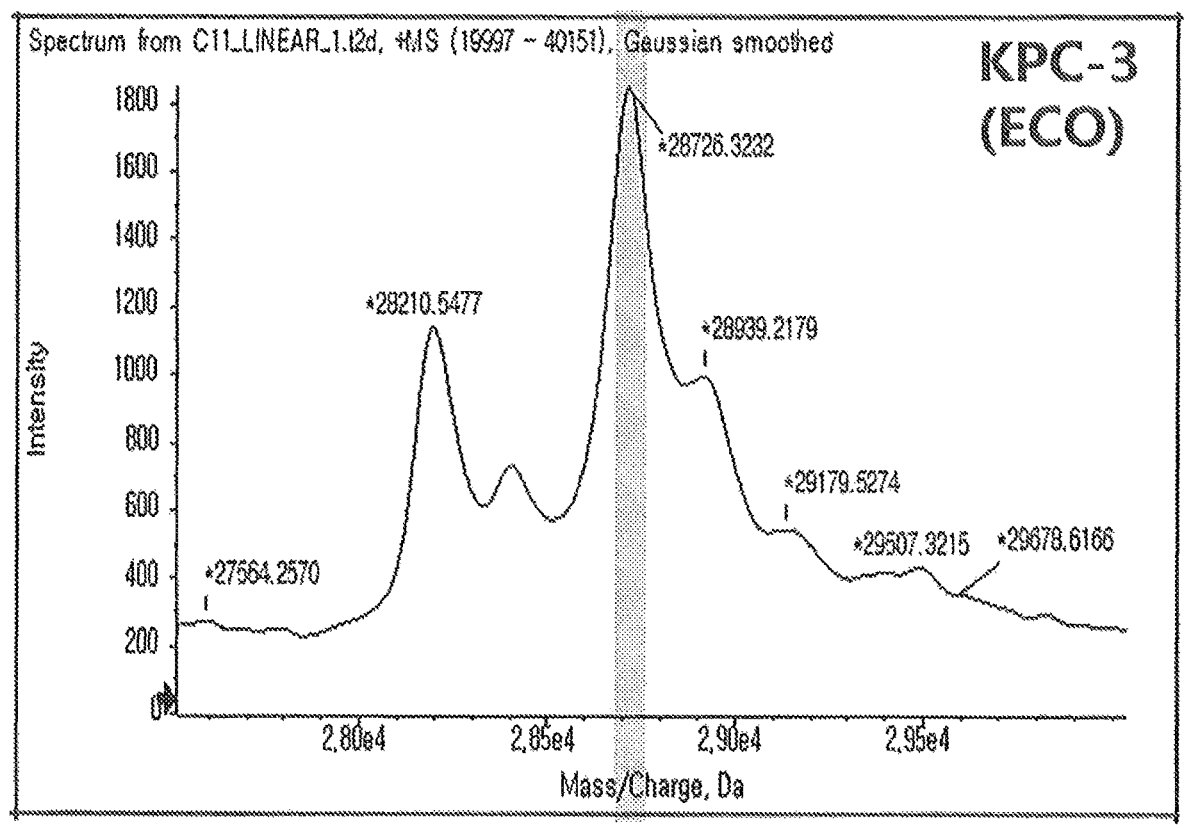
Figure 1F:
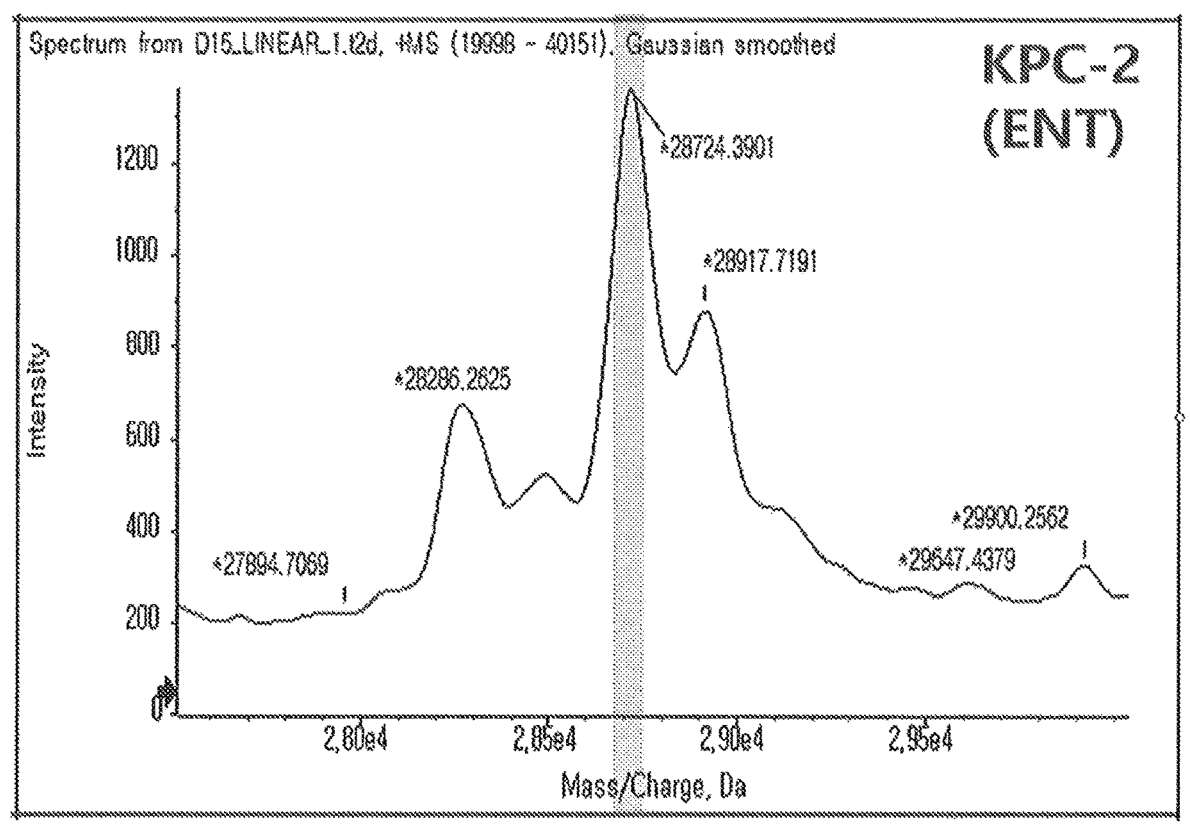
Figure 1G:
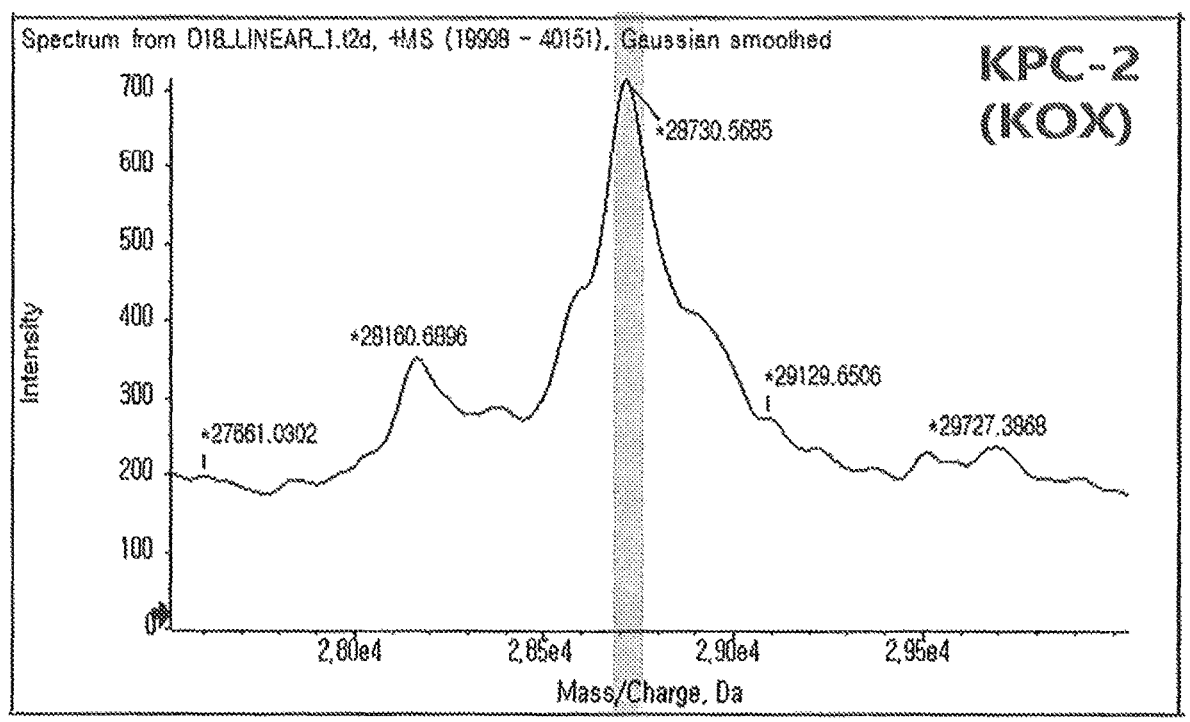
Figure 1H:
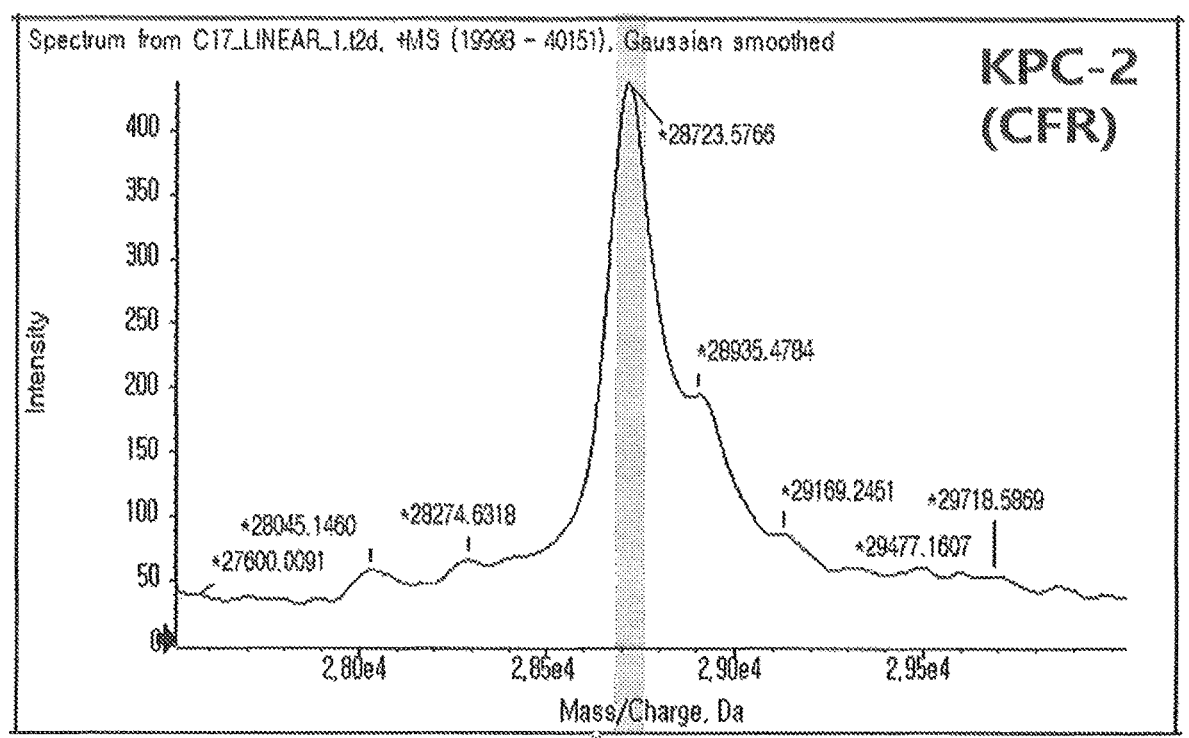
Figure 1I:
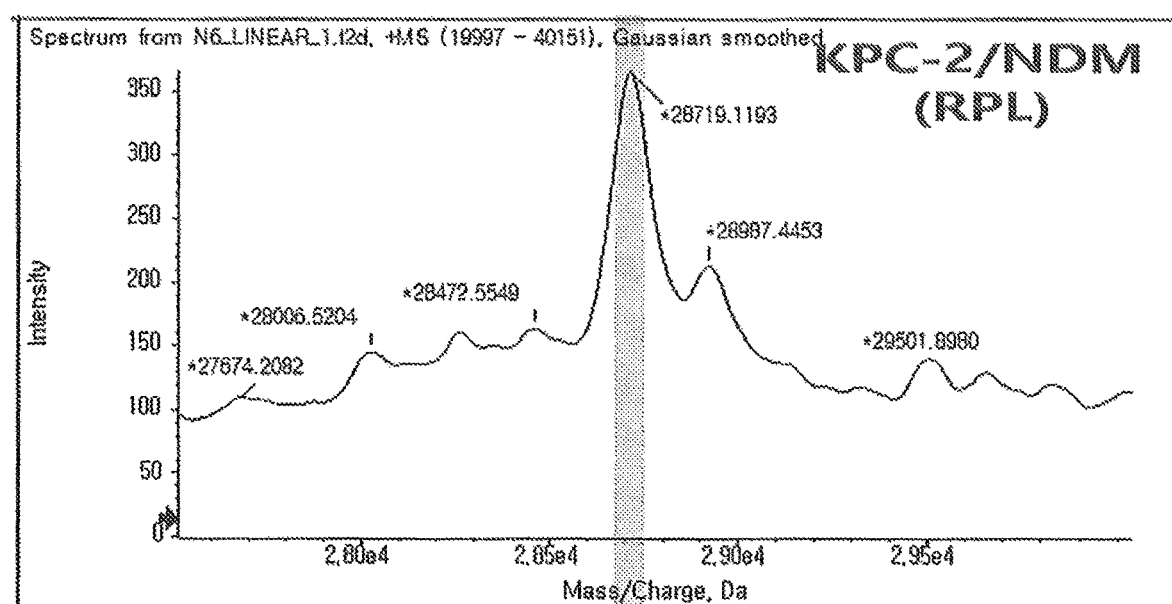
Figure 2A:
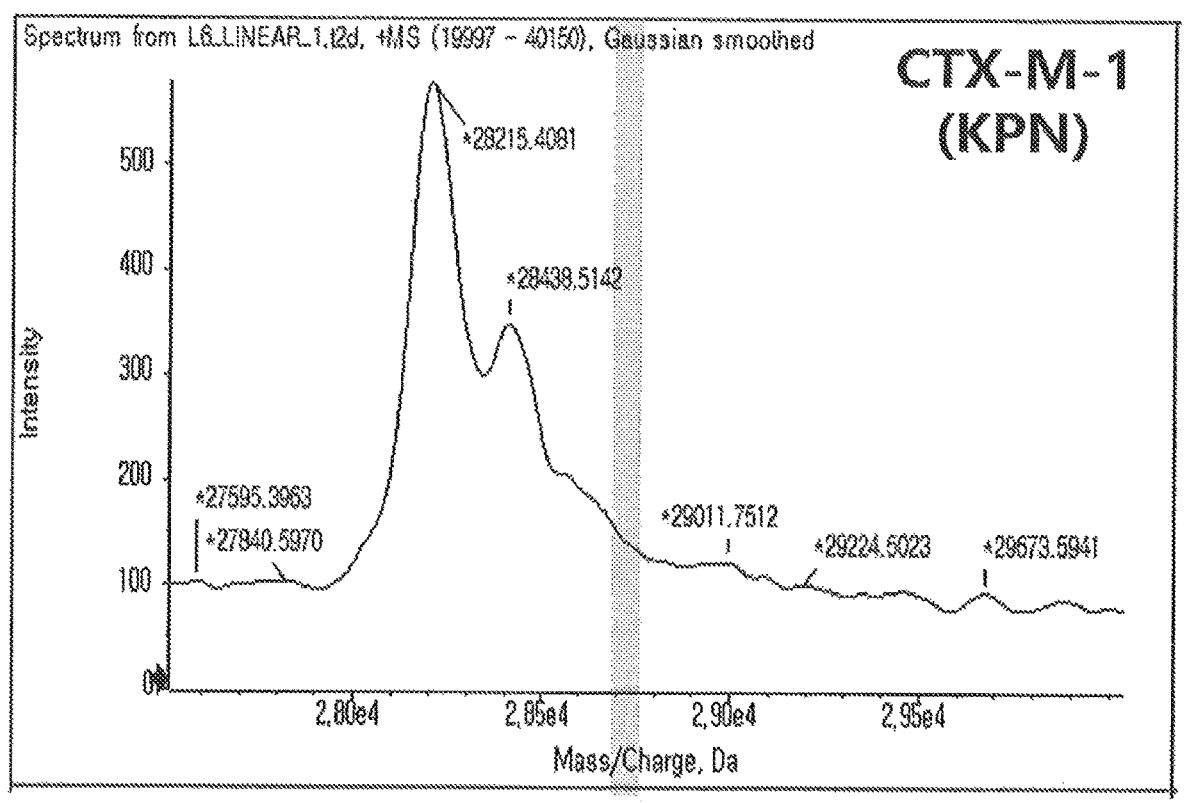
FIG. 2 shows data obtained by identifying a strain, which does not have carbapenemase, using MALDI-TOF according to the method of the present invention using a detergent.
Figure 2B:
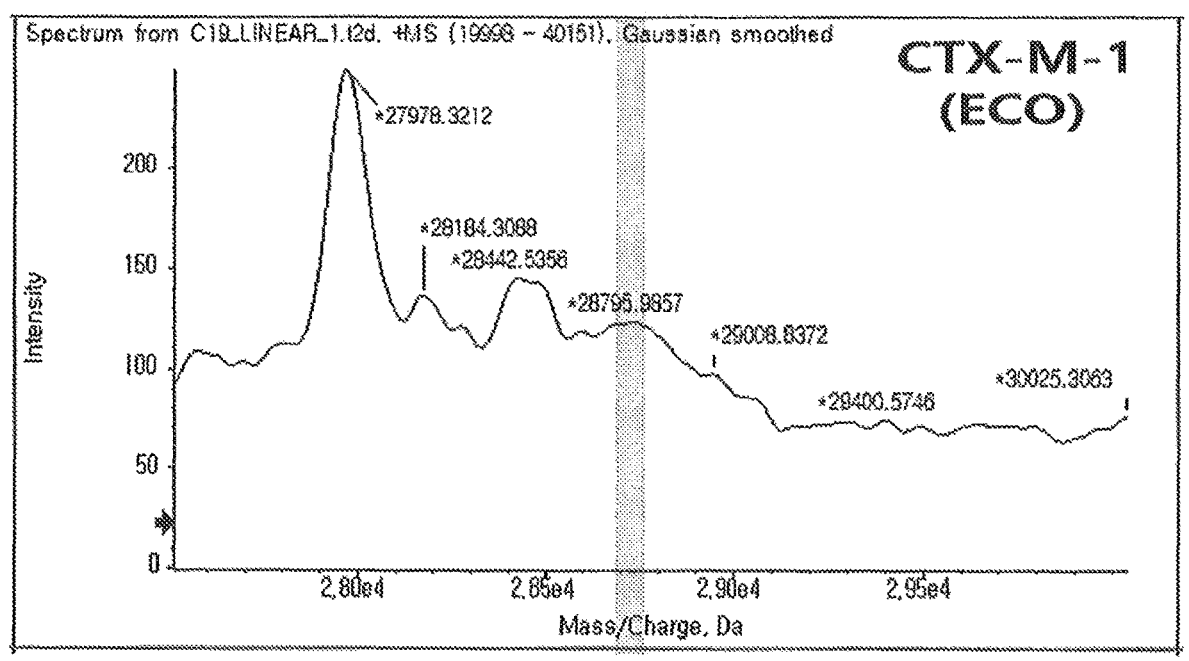
Figure 2C:
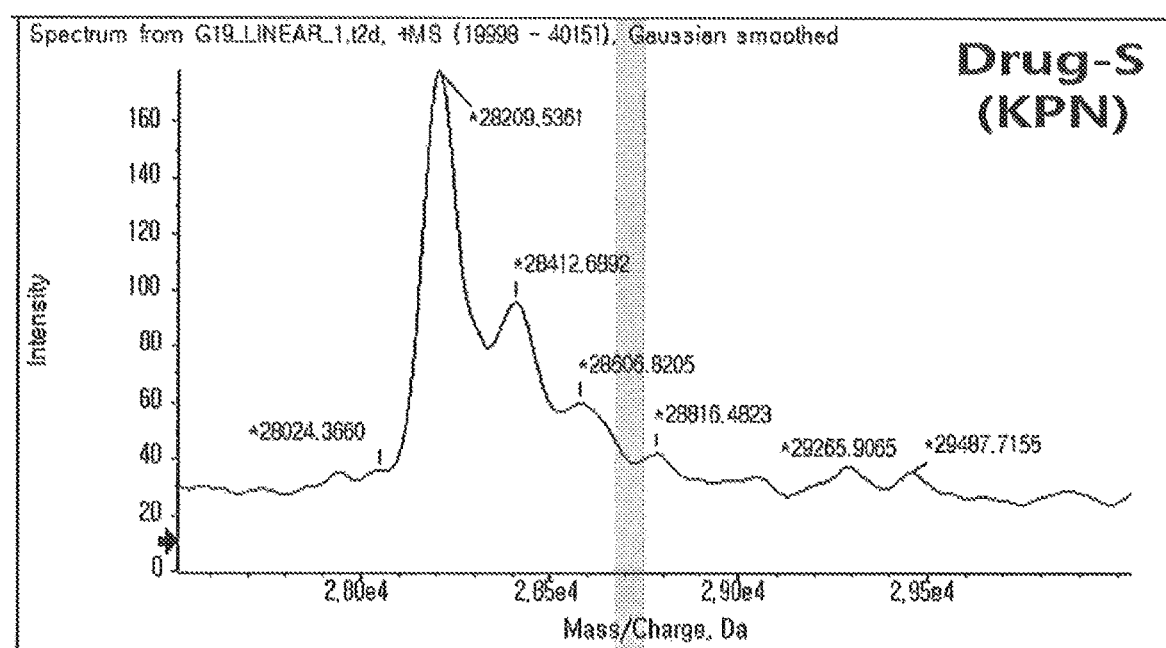
Figure 2D:
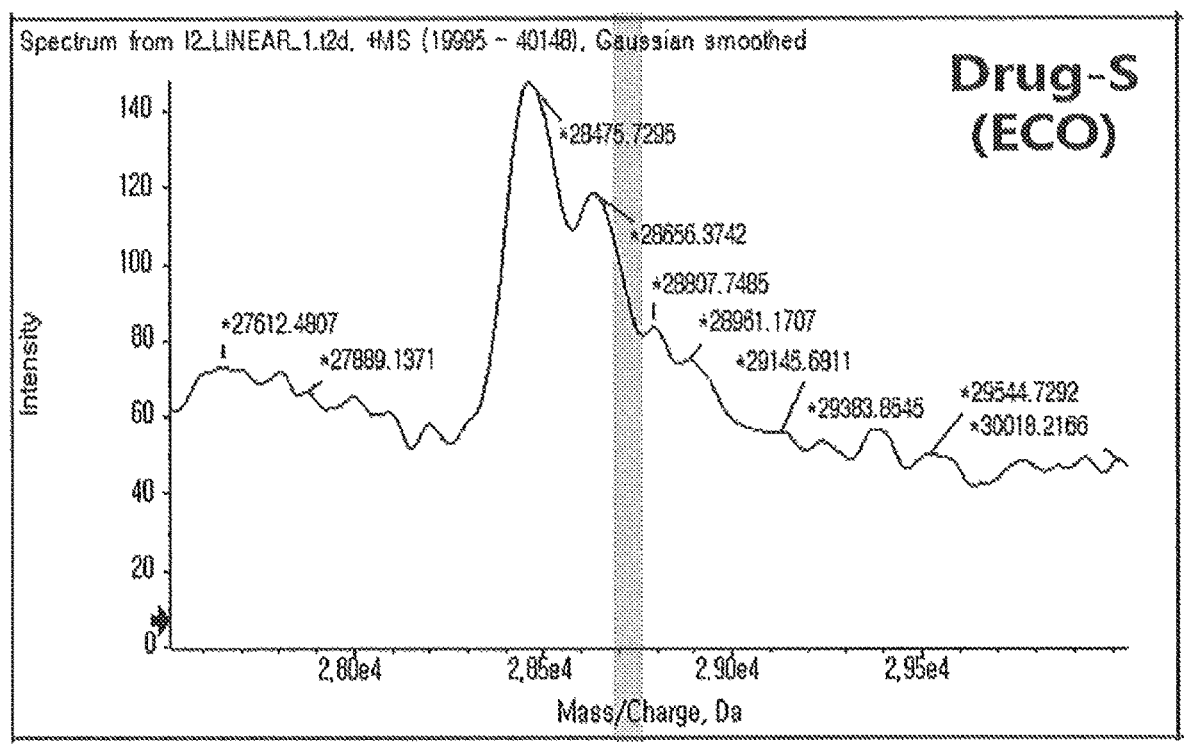
Figure 2E:
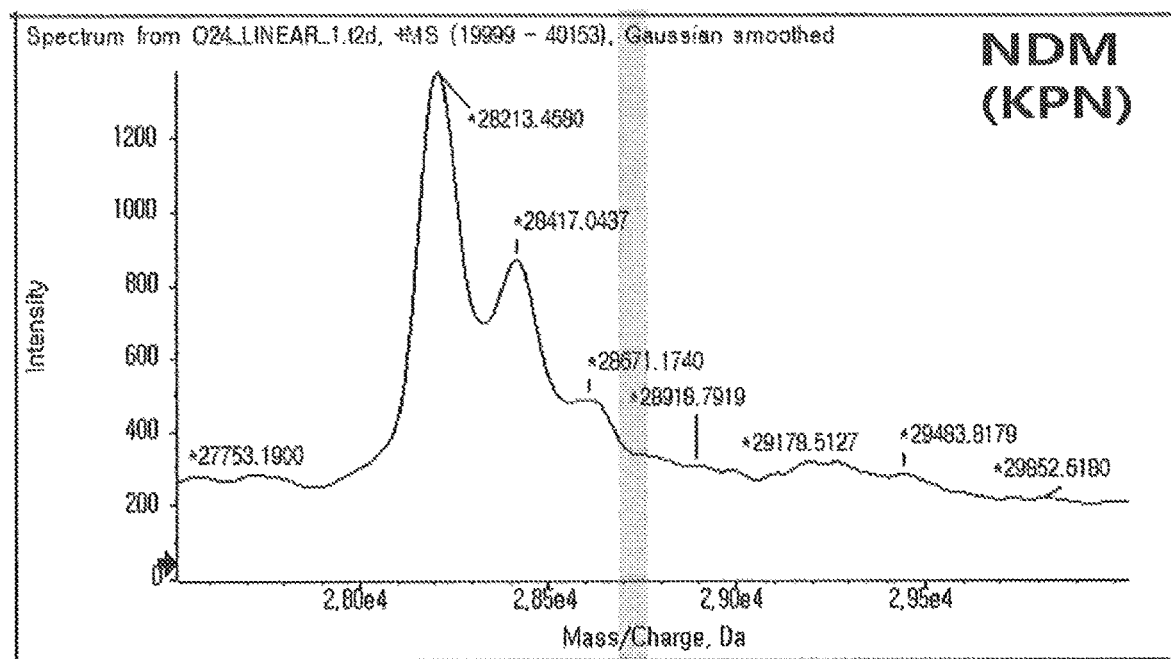
Figure 2F:
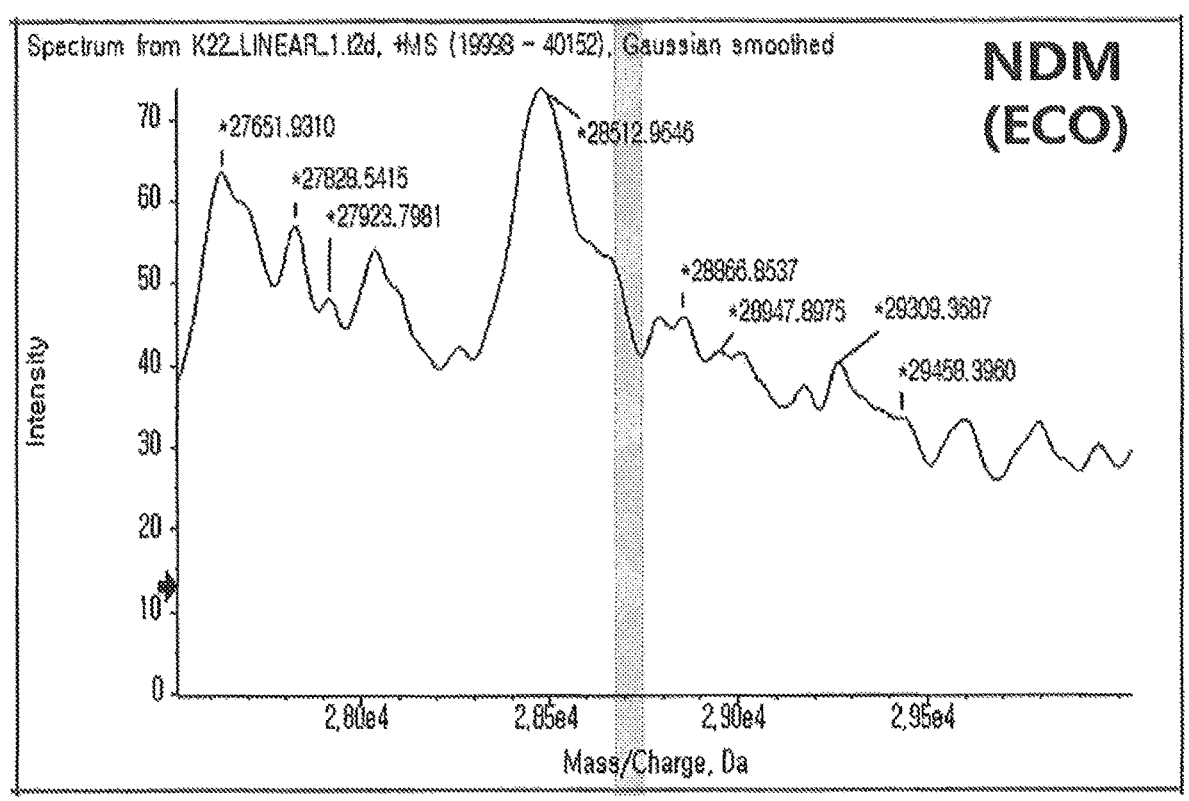
Figure 2G:
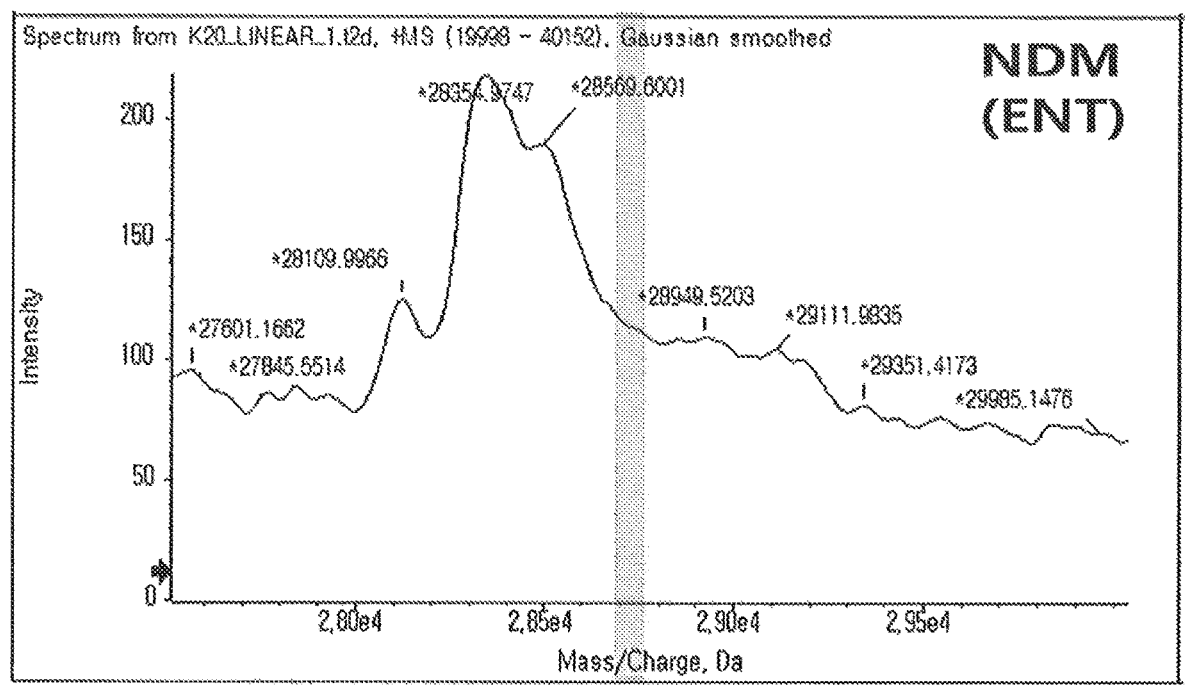
Figure 2H:
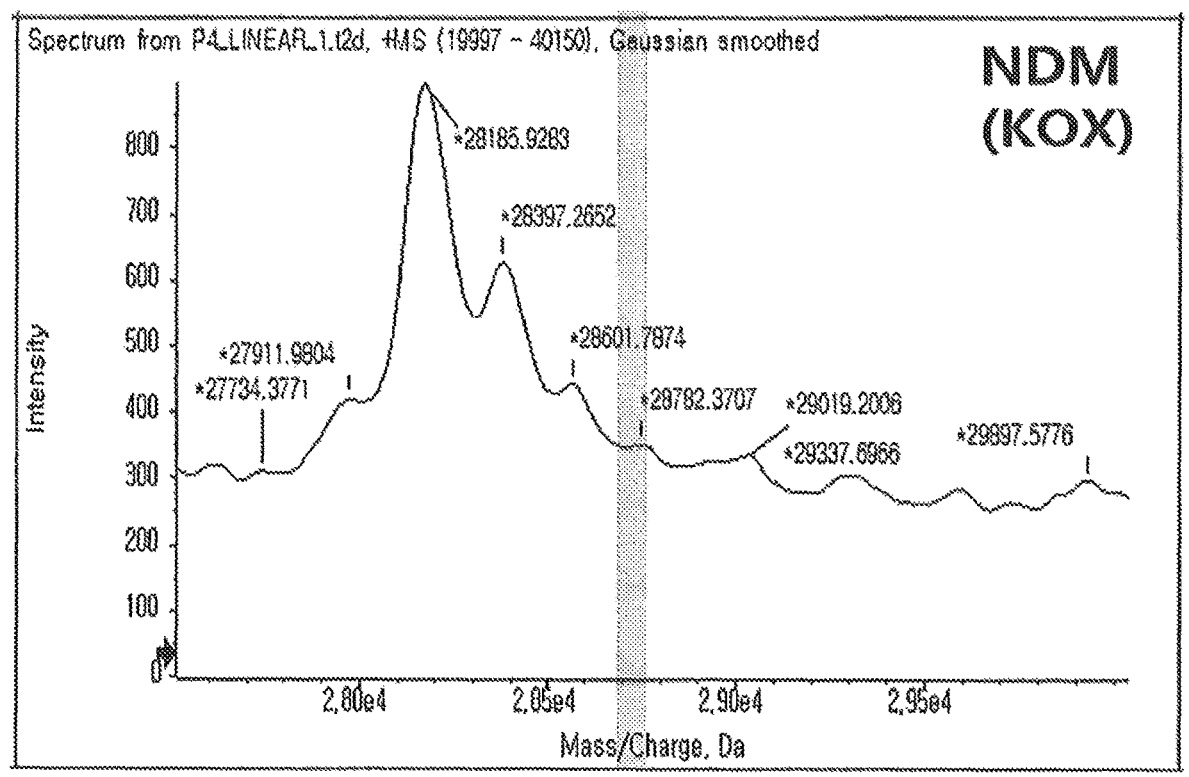
Figure 2I:
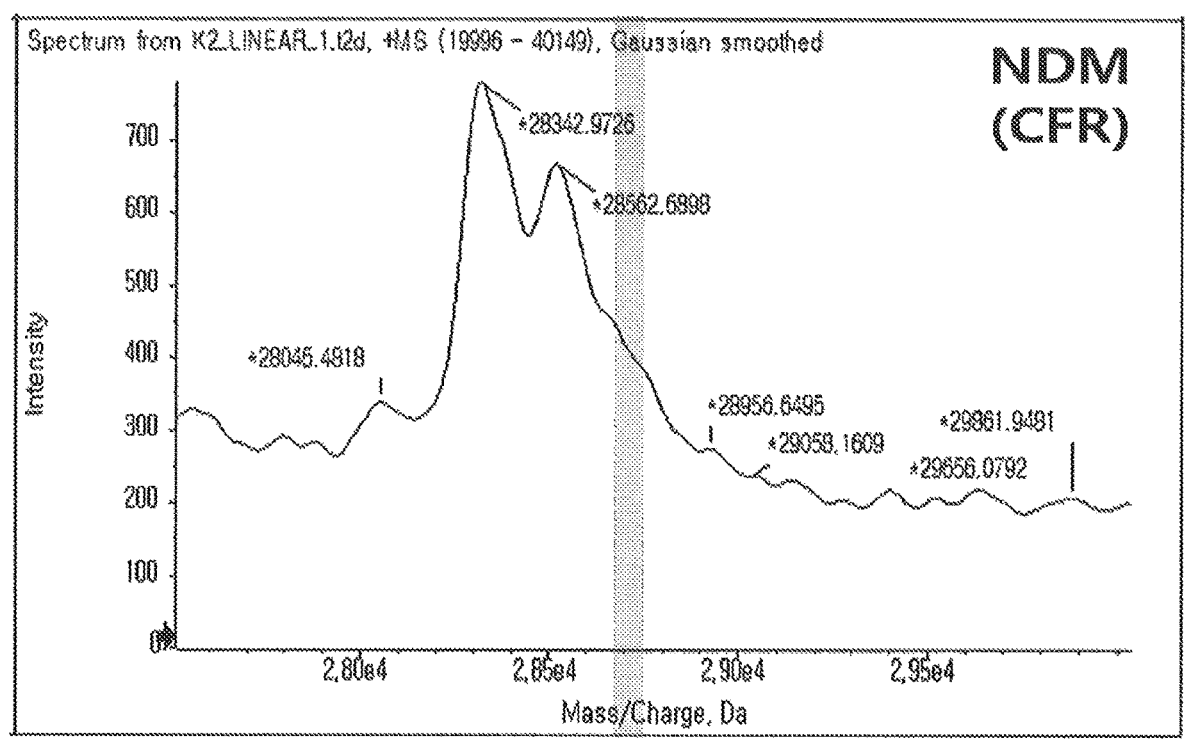

Hereinafter, specific embodiments of the present invention will be described in more detail with reference to Examples.

1. Antibiotic

"Antibiotics" refers to "substances that prevent the growth or generation of microorganisms". Antibiotics may be classified according to the mechanism of action or the antimicrobial zone. The antimicrobial zone means the kind of bacteria antibiotics are effective against. Broadly classifying bacteria, bacteria are classified as gram-negative bacteria or gram-positive bacteria depending on the color to be stained when the bacteria are stained by a method called gram staining, and are classified into rod-shaped rods and ball-shaped cocci depending on the shape thereof. Bacteria are also classified as aerobic bacteria or anaerobic bacteria depending on whether or not oxygen is required for growth and metabolism thereof. In actual clinical practice, gram-positive cocci and gram-negative rods are the most common.

Meanwhile, antibiotics may be harmful to human cells as well as bacteria. Therefore, even helpful antibiotics cannot be used as a therapeutic agent if they also strongly affect human cells. Accordingly, the target of the antibiotic must be present only in the microorganism, or must be essential for the growth or proliferation of the microorganism, but must not be present in human cells. This action that affects only microorganisms is called selective toxicity, and a representative example thereof is a beta-lactam (β-lactam) antibiotic such as penicillin. The beta-lactam antibiotic may be administered safely because the beta-lactam antibiotic inhibits the synthesis of cell walls, which are absent in human cells. Bacteria are surrounded by the structure of cell walls, which are absent in human cells, so that the bacteria can live with bacterial internal pressure that is much higher than the osmotic pressure in the human body. When the synthesis of cell walls is inhibited during each synthesis step of the cell walls, which are essential for the survival of bacteria, bacteria are destroyed. Examples of antibiotics that inhibit the synthesis of bacterial cell walls include beta-lactam antibiotics (penicillin, cephalosporins, monobactam, or carbapenem) and antibiotics such as vancomycin. Antibiotics that inhibit the synthesis of cell walls mainly show antimicrobial activity only against bacteria that are proliferating. The beta-lactam antibiotic is an antibiotic including a beta-lactam ring (β-lactam ring) as a basic structure in a chemical structure. Among the beta-lactam antibiotics, carbapenem is the antibiotic having the broadest antimicrobial zone, and is an antibiotic having favorable antibacterial activity to all of gram-positive bacteria, gram-negative bacteria, and anaerobic bacteria. Imipenem, which has been in use for more than years among the carbapenem series, has drawbacks of hydrolysis in the kidney and side effects in the central nervous system, but recently, meropenem has been developed to overcome these drawbacks. These series of antibiotics are actually the last antibiotics to use when infection by Enterobacteriaceae is suspected. Therefore, when bacteria resistant to these antibiotics appear, it can be said to be a condition of utter defenselessness.

2. Antibiotic Resistance

In recent years, outbreaks of carbapenem-resistant Enterobacteriaceae (CRE) have continued, mainly afflicting patients of domestic university hospitals, and concerns have been raised that CRE may become naturalized and difficult to manage. The naturalization of CRE, which is a superbacterium resistant to almost all antibiotics, has a serious problem in that infection control is very difficult.

Carbapenem is an antibiotic that is used as the last defense against infection by Enterobacteriaceae as described above. Accordingly, the antibiotics used when infection with Enterobacteriaceae resistant to carbapenem antibiotics occurs are extremely limited, which makes it difficult to treat patients and which is very likely to lead to the death of patients.

Mechanisms of causing the antibiotic resistance of these antibiotic-resistant strains are classified into five major categories, namely inactivating the antibiotic, modifying the cell surface on which the antibiotic acts, bypassing biochemical metabolic pathways interfered with by the antibiotic, immediately expelling antibiotic materials, and forming an environment in which specific antibiotics do not work. Among the mechanisms, with respect to the mechanism for inactivating the antibiotic, a strain that secretes an enzyme hydrolyzing the antibiotic to thus incapacitate the antibiotic is called carbapenemase-producing Enterobacteriaceae (CPE).

CPE secretes a hydrolase that decomposes the beta-lactam ring of the beta-lactam antibiotic, thus inactivating the beta-lactam antibiotic. The mechanism whereby gram-negative rods acquire carbapenem resistance is classified according to production of class A, class B, and class D hydrolases.

GES, KPC, SME, IMI, and NMC-A are known as class A carbapenemase, and KPC and GES are most commonly reported. KPC has recently emerged as the world's most common cause of carbapenem resistance, and the rate of carbapenem antibiotic resistance of *K. pneumoniae* has increased worldwide in the recent decade since the occurrence of KPC.

Class B carbapenemase has hydrolytic activity against most beta lactam antimicrobials such as penicillin, cephalosporin, and carbapenem, and an IMP type, a VIM type, an SPM type, a GIM type, a SIM type, an NDM Type, an AIM type, a KHM type, and a DIM type are reported as representative examples thereof. In recent years, the global spread of gram-negative bacilli producing NDM-1 has been considered a problem.

The class D type shows strong activity in hydrolysis of oxacillin. Accordingly, the class D type is classified as an OXA type, and about 200 kinds or more are known to date.

3. Direct Detection of Carbapenemase

Meanwhile, the present invention provides a method for quickly and easily confirming whether the strain belongs to the CPE among the CREs. Accordingly, an antibiotic therapy for inhibiting microorganisms as a mechanism different from that of the carbapenem antibiotic may be applied to a strain that is determined to be a CPE, thereby achieving rapid and precise treatment of antibiotic-resistant strains.

More specifically, the present invention provides a method capable of directly detecting the carbapenem hydrolase secreted by the CPE. The carbapenem hydrolase to be identified is preferably KPC, NDM, or OXA. As an identification method, a mass-spectrometry method is used. Preferably, a mass-spectrometry method using MALDI-TOF is used.

The above-described identification method may be compared with a nucleic acid amplification method as a conventional identification method (for example, real-time PCR). In the case of the nucleic acid amplification method, limited genetic information of the carbapenem hydrolase is provided as described above in order to indirectly determine whether carbapenem is present. However, even when a false signal for detecting a gene derived from an enzyme that has actually lost the carbapenem decomposition activity due to a mutation is included therein, there is no way to confirm the false signal. Therefore, there is a problem of reliability.

Meanwhile, there are also known techniques for identifying carbapenem hydrolase using a mass-spectrometry method. However, all of them are methods of decomposing the target enzyme into peptide units and then individually detecting the peptides, and a method of directly detecting the carbapenem hydrolase in an intact form is not yet known. The above-described methods of decomposing the carbapenem hydrolase into peptide units followed by analysis are very complicated and require several days to obtain the identification result, thus having a problem in that it is not possible to provide appropriate treatment to a patient in a timely manner. Further, the method of determining the presence or absence of an enzyme indirectly through fragment information has a problem of reliability, as in the nucleic acid amplification method described above, which cannot be ignored. Accordingly, the present inventors have proposed a method of directly detecting the carbapenemase secreted by CPE using a popular mass spectrometer. The method has a merit in that whether antibiotic resistance occurs is determined in a time as short as a dozen minutes, thus quickly providing appropriate treatment

4. Pretreatment Method for Direct Detection of Carbapenemase

In order to directly detect carbapenemase, first, carbapenemase must be completely separated from the strain. However, there is a problem in that the location where the carbapenemase is distributed in the cell structure has not yet been clearly elucidated. In other words, whether carbapenemase is present in the bacterial cell membrane or in the cytoplasm is not clear. Accordingly, in the conventional technology, attempts have been made to indirectly detect whether the target enzyme is present by randomly decomposing all proteins of the cell using a protease and then collecting fragments composed of desired sequences. However, as described above, this indirect method has a problem of reliability.

In order to overcome the problems with the conventional technology, the present inventors have applied a pretreatment method in which a site where carbapenemase may be present is targeted, followed by lysing. In particular, the present inventors have applied a pretreatment method in which the bacterial cell membrane is targeted in order to obtain proteins in an intact form in the cell membrane.

Specifically, an amphiphilic detergent may be used to separate proteins from bacterial cell membranes.

The cell membrane has a bilayer structure in which the phospholipid, which includes a hydrophilic head and a hydrophobic tail, including two strands of hydrocarbon chains, is arranged so as to form two layers, and contains a membrane protein in patches therebetween. The membrane protein is maintained in the cell membrane due to a hydrophobic interaction between hydrophobic hydrocarbon chains of the phospholipid and hydrophobic domains of the protein.

Meanwhile, a detergent molecule includes a hydrophilic head and a hydrophobic tail, and has a structure very similar to the phospholipid in the cell membrane, thereby mimicking the phospholipid and lysing the protein. The micelle formed due to aggregation of the detergent molecules is very similar in structure to the phospholipid bilayer of the cell membrane, and thus, like the phospholipid bilayer, proteins may be contained in the micelle due to the hydrophobic interaction. Accordingly, the membrane proteins in the cell membrane may be trapped in the micelle structure of the detergent, so that the membrane proteins leave the cell membrane, thus being eluted in a solution (buffer). Further, the cell membrane may be destroyed in this process, and thus proteins that are present in a floating state in a periplasm between the cell membrane and the cell wall may be eluted.

In the present invention, based on the mechanism of lysing the protein of the detergent, the protein may be separated in an intact form from the bacterial cell membrane. Accordingly, when the carbapenemase is present in the protein released from the cell membrane, the active type thereof may be detected in an intact state using a mass spectrometer.

The detergent is classified into an ionic detergent and a non-ionic detergent according to the ionic characteristics of the head in a molecular structure thereof.

Meanwhile, the mass spectrometer is based on a basic principle in which the distance that the charged particles reach in a magnetic field is measured, and is a measuring device that is very susceptible to the degree of ionization of the target sample. Therefore, the ionic detergent inevitably affects the ionization of the sample of the mass spectrometer, and thus is not suitable for use in the target sample of the mass spectrometry. For this reason, the use of detergents as pretreatment for the mass-spectrometry method has been eliminated in the conventional technology. This is because it is almost impossible to provide the detergent at a level that will not affect the results in the analysis step after the pretreatment. This knowledge in the art is applied to non-ionic detergent, and there are no examples of non-ionic detergents used in the pretreatment step of samples for mass spectrometry.

Meanwhile, in the present invention, a non-ionic detergent may be preferably used as a detergent for lysing the target sample of mass spectrometry.

Non-ionic detergents have very diverse types, and cyclohexyl-n-hexyl-β-maltoside, n-decanoylsucrose, n-dodecanoylsucrose, n-decyl-β-maltopyranoside, n-dodecyl-β-glucopyranoside, n-dodecyl-β-maltoside, n-heptyl-β-D-glucopyranoside, n-heptyl-β-D-thioglucopyranoside, n-hexyl-β-D-glucopyranoside, n-nonyl-β-D-glucopyranoside, n-octanoylsucrose, n-octyl-β-D-glucopyranoside, n-octyl-β-D-maltopyranoside, n-octyl-β-D-thioglucopyranoside, OGNG (octyl glucose neopentyl glycol), and saponin are used. Among them, OG (n-octyl-β-D-glucopyranoside), OTG (n-octyl-β-D-thioglucopyranoside), DDM (n-dodecyl-β-D-maltopyranoside), OGNG (octyl glucose neopentyl glycol), and DDTM (n-dodecyl-β-D-thiomaltopyranoside) may be preferably used.

Meanwhile, in the present invention, a step of performing sonication may be optionally performed in the pretreatment step. Specifically, the cultured bacteria strains may be homogenized in a solution containing a buffer, and the homogenized sample may be sonicated at room temperature to thus release the desired protein in an intact state.

MODE FOR INVENTION

Example

In order to detect an active form of carbapenemase in an intact state, the present inventors first performed a typical antimicrobial sensitivity test on the collected strains, confirmed the sensitivity, confirmed the genotype of the carbapenemase of the antimicrobial resistant strains using a molecular genetic method, and investigated the molecular dynamic properties of resistant bacteria, thus obtaining transconjugants of KPC, NDM, and OXA. In addition, accurate actual data of the carbapenemases were obtained through actual measurement. In addition, the measurement values measured using MALDI-TOF on the unknown strains were compared to the above-described data, thereby inventing a method of confirming whether the target strain is a strain producing carbapenemase, that is, a strain resistant to carbapenem.

1. Typical Antibiotic Sensitivity Test

The antimicrobial sensitivity of the collected strain was confirmed using a disk diffusion method recommended by CLSI. The test strain was subjected to subculturing on MacConkey agar, and one independent colony was collected using a platinum needle, followed by inoculation in a Tryptic soy broth so that the turbidity was set at a McFarland no. of 0.5. After a Mueller-Hinton agar was inoculated with a bacterial suspension solution using a cotton swab, an antimicrobial disc was placed thereon. The medium inoculated with bacteria was cultured in a constant-temperature oven at 37° C. for 18 hours, and the size of the inhibition zone formed around each antimicrobial disc was measured. For accuracy of the result, the sensitivity of *E. coli* ATCC 25933, as a control strain, was also tested.

2. Test for Confirming Genotype of Carbapenemase Using Molecular Genetic Method

The genotype of carbapenemase was confirmed by PCR using the designed primer. 5 µl of DNA extract of the test bacteria, 1 µl of each primer, 2.65 mM (8 µl) of deoxynucleotide triphosphate, 10 µl of a 10×buffer, and 75.5 µl of distilled water were mixed with each other to manufacture a PCR reaction solution. Thirty cycles of PCR, including denaturation using Gene Amp PCR System 9600 (Perkin-Elmer Centus Corp., Norwalk, Conn., USA) at 94° C. for 30 seconds, annealing at 60° C. for 30 seconds, and extension at 72° C. for 30 seconds, were performed. 3 µl of the amplified product was subjected to electrophoresis in a 2.0% agarose gel for 20 minutes to thus confirm a band of the amplified product. The PCR amplified product was extracted to analyze a sequence in both directions using a Sequence Version 2.0 DNA sequencing kit (U.S., Biochemicals, Cleveland, Ohio, USA).

3. Investigation of Molecular Dynamic Properties of Resistant Bacteria: Multi-Locus Sequence Typing (MLST)

The investigation was performed in order to analyze the long-term dynamic association of some multiple-drug-resistant strains. After sequencing several major genes involved in the intracellular metabolism of the test bacteria, the data were input into the MLST database via the Internet for the purpose of analysis.

4. Pretreatment of Sample 4-1) Pretreatment of Sample Using Detergent

Strains were cultured using a sample collected from a patient, for example, blood, sputum, intraoral mucosa, secretions, urine, or body fluids. For a culture medium, an agar plate medium, such as an agar plate, an MCP (MacConkey agar plate), an LB agar, and a blood medium, may be used.

The cultured bacteria strains were lysed in a lysis buffer. A feature of this pretreatment method is that the lysis buffer includes a non-ionic detergent. Accordingly, the desired target protein (hydrolase) may be directly separated from the cell membrane and detected in an intact state, without randomly decomposing the protein of the target sample into peptide units. Therefore, a protease inhibitor may be added if necessary.

Subsequently, the lysed sample was subjected to vortexing and incubating and then centrifugation using a centrifuge at room temperature. A supernatant was isolated and collected after the centrifugation.

4-2) Pretreatment of Sample Using Sonication

The culture of the strain was the same as in the pretreatment of 4-1, and the cultured bacteria strains were then homogenized in a buffer.

*

*Subsequently, the sample was sonicated. The sonication was performed at room temperature.

The pretreated sample was subjected to centrifugation using a centrifuge at room temperature. A supernatant was isolated and collected after the centrifugation.

5. Identification of Carbapenem Hydrolase Using Mass Spectrometry

The supernatant obtained in the last step of the pretreatment process was dropped on a plate for mass spectrometry and was then dried at room temperature. In the present invention, analysis was performed using a MALDI-TOF mass spectrometer. A matrix for MALDI-TOF analysis was dropped on the dried sample, and additional drying was then performed.

After the matrix was completely dried, the target plate was subjected to mass spectrometry using MALDI-TOF.

6. Data Confirmation

Subsequently, by confirming the peak value of the obtained data, it is possible to directly confirm whether a target protein, that is, a carbapenemase to be detected, is present.

For example, in the case of strains having an enzyme corresponding to the genotype of KPC, among the carbapenemases, it could be confirmed that all of them exhibited a strong peak around m/z of about 28,670 to 28,770. Further, in the case of strains having an enzyme corresponding to the genotype of OXA, it could be confirmed that all of them exhibited a strong peak around m/z of about 28,100 to 28,200.

Example 1: Identification of KPC Through Pretreatment Using Detergent

The sample obtained through the pretreatment method of 4-1 was identified using MALDI-TOF, and the results are shown in FIGS. 1 and 2.

First, referring to FIG. 1, it can be confirmed that all of KPN (*Klebsiella pneumoniae*), ECO (*E. coli*), ENT (*Enterobacter* spp.), KOX (*Klebsiella oxytoca*), CFR (*Citrobacter freundii*), and RPL (*Raoultella planticola*) strains having an enzyme corresponding to the genotype of KPC among the carbapenemases exhibit a strong peak around m/z of about 28,670 to 28,770. The peak values are peak values corresponding to KPC.

In contrast, referring to FIG. 2, showing the measurement results for the strains that did not have KPC, no peak was observed around m/z of about 28,670 to 28,770, corresponding to the KPC peak value. For reference, "Drug-S" represents a strain that is susceptible to all beta-lactam antibiotics (even penicillin), and "CTX-M" represents a strain that is resistant to most beta-lactam antibiotics but is not resistant to carbapenem. None of these strains expressed KPC, among the carbapenemases, and thus the peak thereof did not appear in mass spectrometry.

Figure 3A:
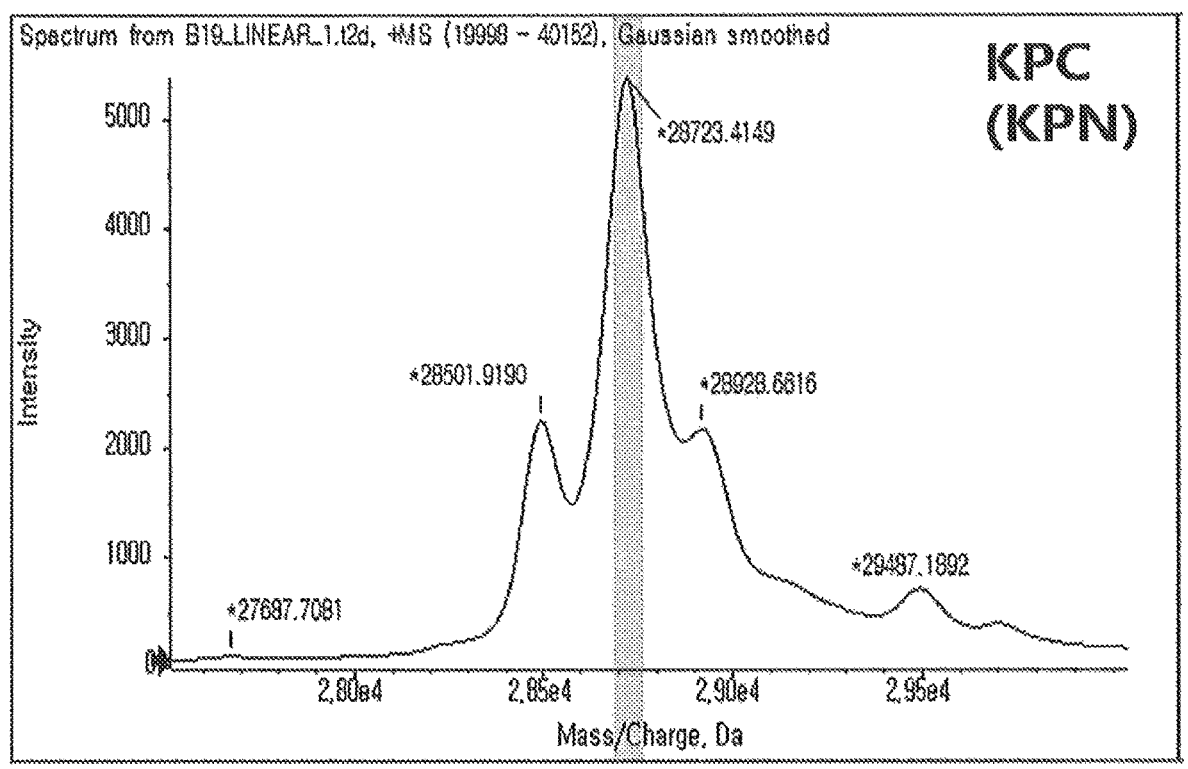
FIG. 3 shows data obtained by identifying a strain, which is genetically recombined to have carbapenemase, using MALDI-TOF according to the method of the present invention using a detergent.
Figure 3B:
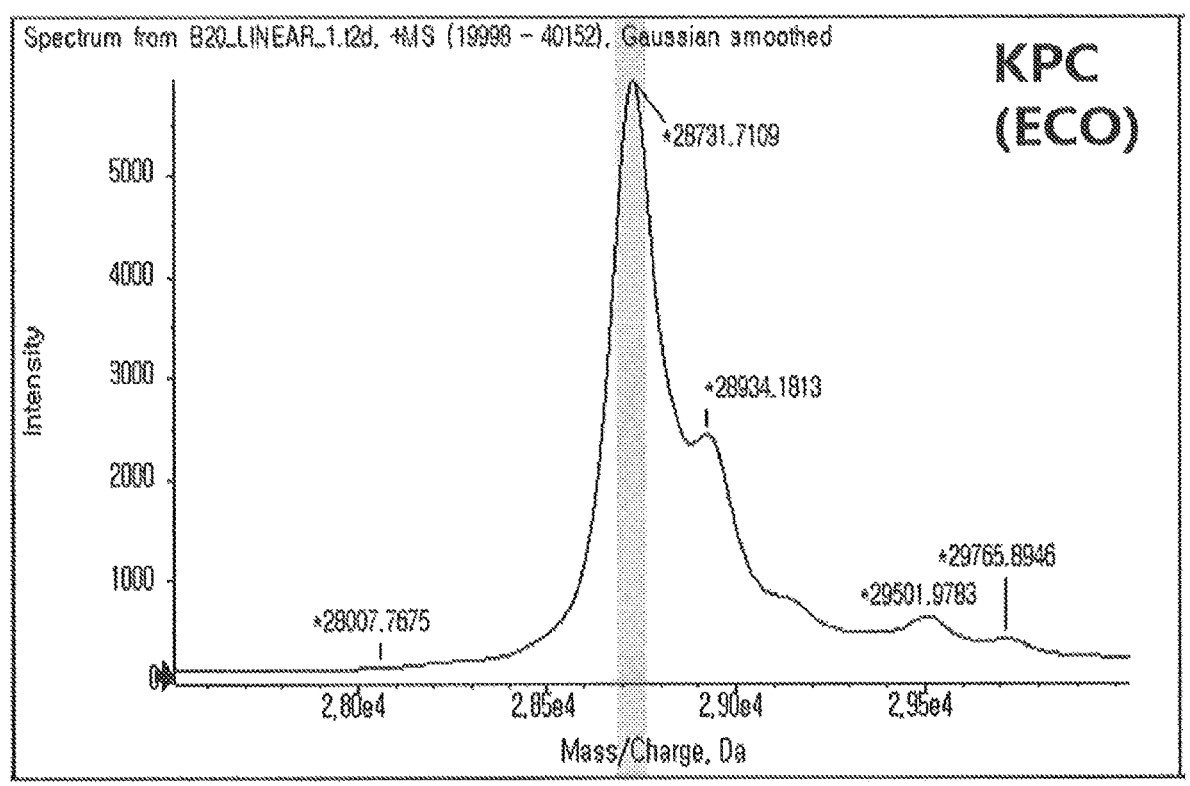

Meanwhile, the measurement of the strains recombined so as to express KPC was performed, and the result is shown in FIG. 3. These strains also exhibited a strong peak around m/z of about 28,670 to 28,770. Accordingly, it could be confirmed that KPC was easily identified using a mass spectrometer according to the method of the present invention.

Figure 5:
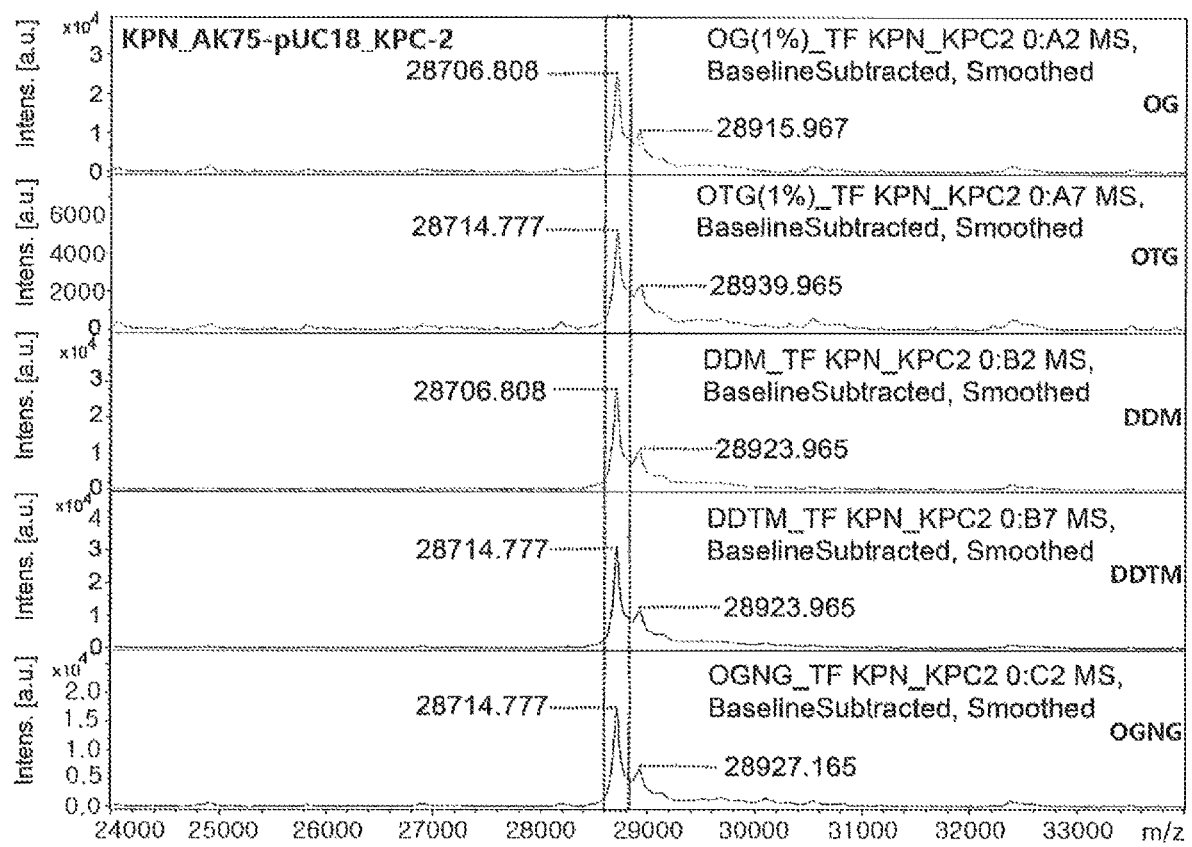
FIG. 5 shows MALDI-TOF identification data for the genetic-recombinant strain expressing carbapenemase KPC, which are measured while changing a detergent.
Figure 6:
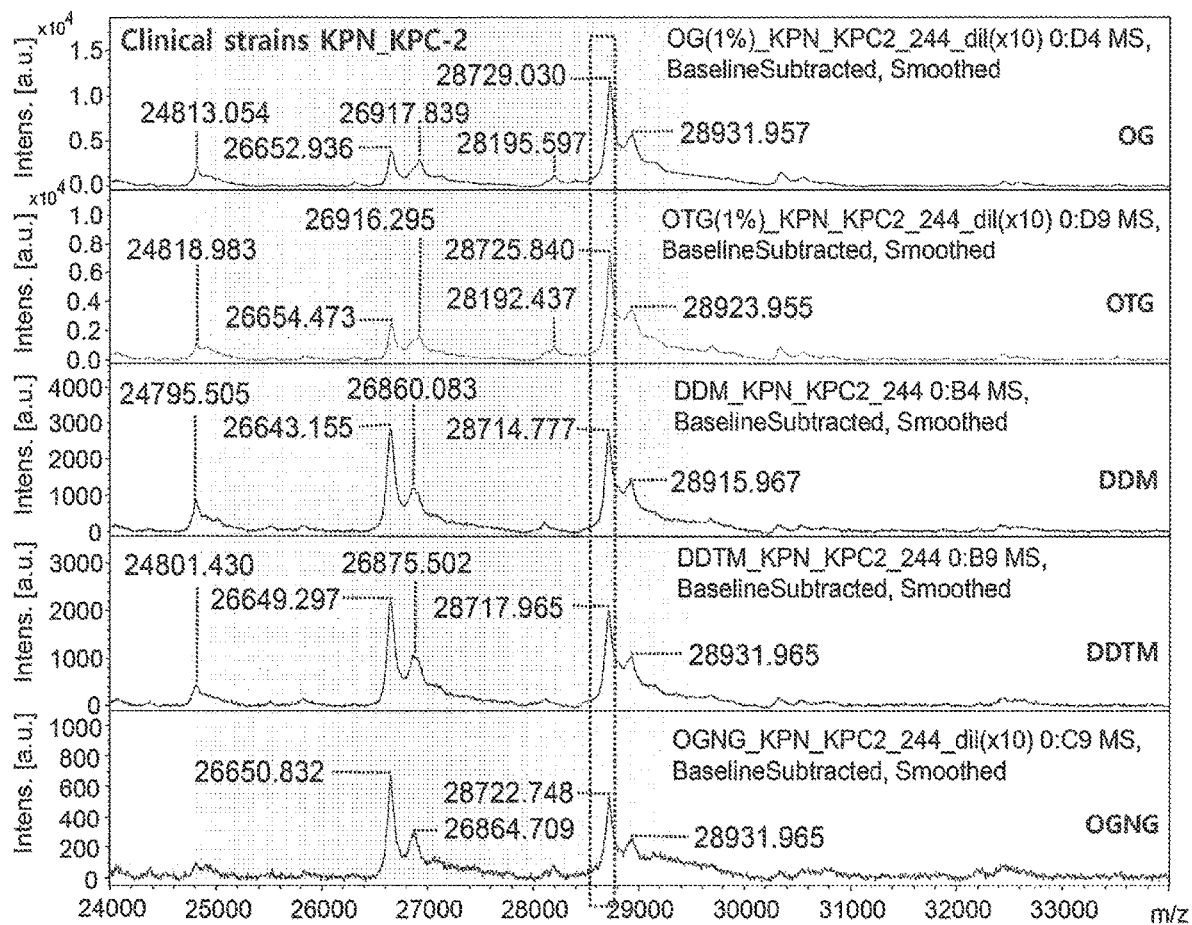
FIG. 6 shows MALDI-TOF identification data for the clinical strain expressing carbapenemase KPC, which are measured while changing a detergent.

Moreover, the KPN strains expressing KPC were subjected to mass spectrometry using the same method with different detergents, and the results are shown in FIGS. 5 and 6 (the concentrations of the detergents were the same, namely 1%). Both the measured value of the clinical strain expressing KPC which is a positive control group (FIG. 6) and the measured value of the strain recombined so as to express KPC (FIG. 5) indicate strong peaks around m/z of about 28,670 to 28,770.

Example 2: Identification of OXA-48 Through Pretreatment Using Detergent

Figure 4:
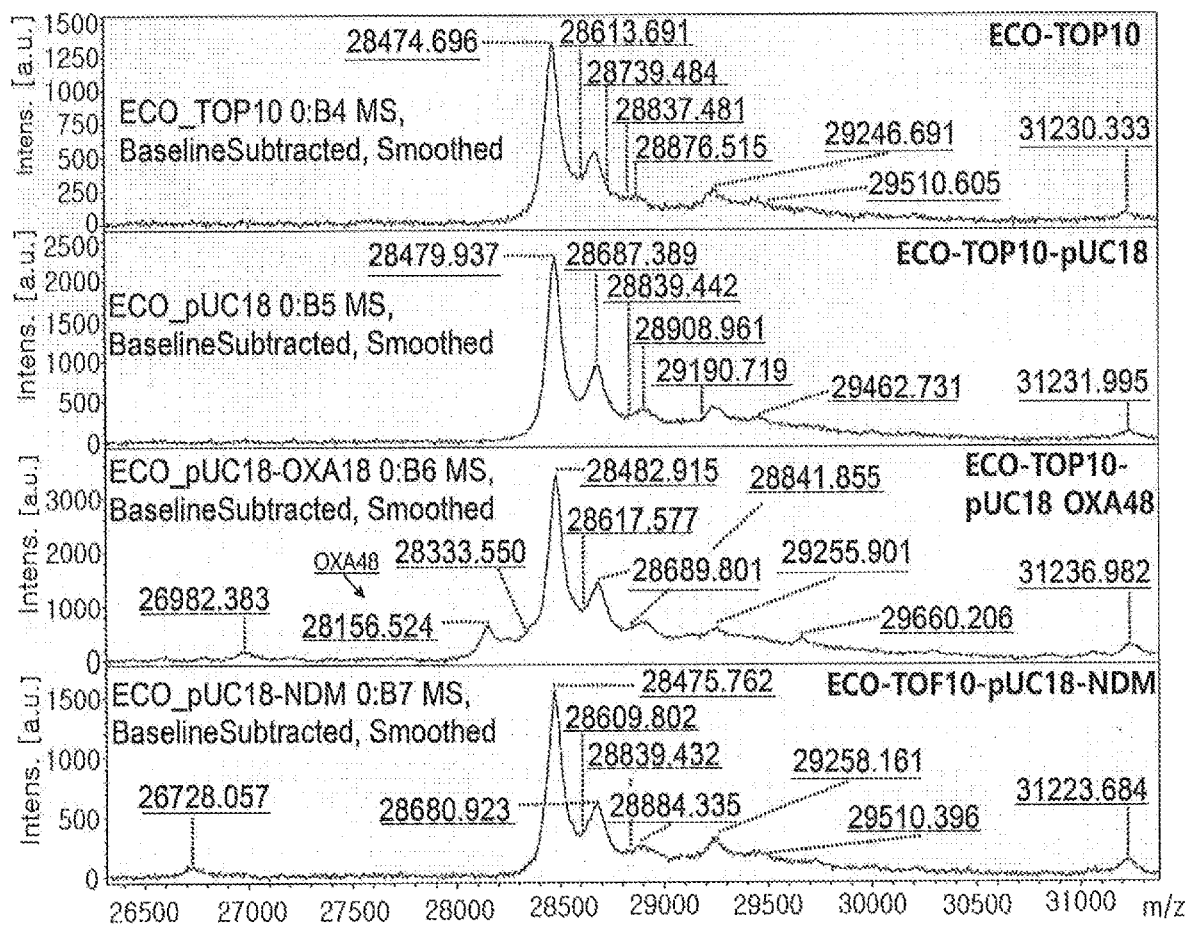
FIG. 4 shows MALDI-TOF measurement data of recombinant *E. coli*.

OXA-48, which is another genotype of carbapenemase, was subjected to the same experiment, and the result is shown in FIG. 4. The peak that was not seen in an *E. coli* TOP10 or *E. coli* TOP10-pUC18 strain (FIGS. 4a and 4b) that did not express OXA-48 was observed in a strain expressing OXA-48 (peak at m/z of 28156.524 in FIG. 4c) but was not observed in a strain expressing NDM instead of OXA-48 (see FIG. 4d). The corresponding peak in FIG. 4 means direct detection of the active form of the OXA-48 protein.

Example 3: Direct Pretreatment on Colony Plate

Figure 7:
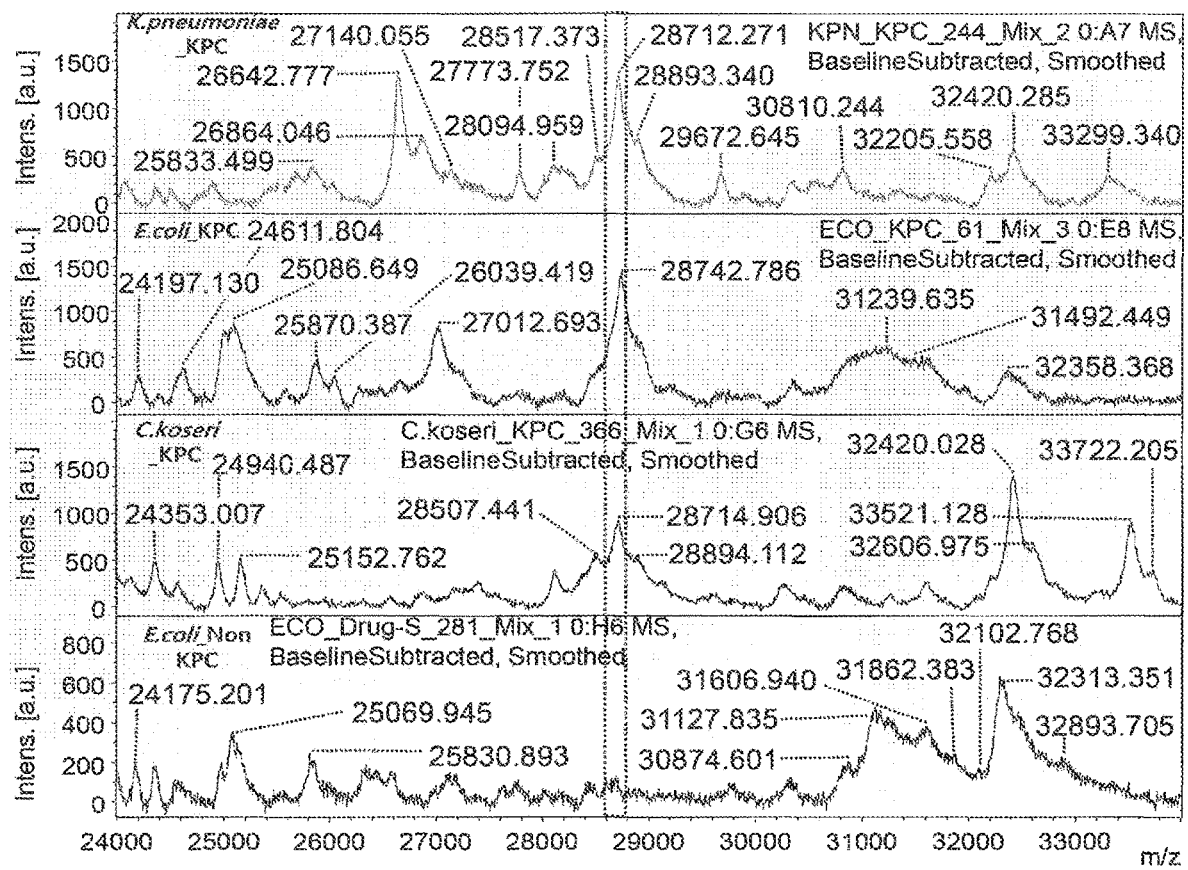
FIG. 7 shows data obtained by directly treating samples on a plate of a mass spectrometer, followed by identification using MALDI-TOF.

The same experiment as in Example 1 was directly performed on a plate for a mass spectrometer. Specifically, the strain to be tested was cultured one day before the test (37° C. incubation) on the agar plate medium (agar plate, MacConkey plate, LB agar, or blood medium). One colony of bacteria strains grown on the agar medium was thinly applied on the spot of the plate for the mass spectrometer. A lysis buffer containing 1 µl of a detergent was placed on the spot on which the colony was applied, and the buffer and bacteria were mixed using a pipette. 1 µl of the matrix was dropped on the completely dried sample and was then dried. After the matrix was completely dried, measurement was performed using the MALDI-TOF equipment, and the KPC peak was confirmed. The result is shown in FIG. 7.

A strong peak was confirmed around m/z of 28,670 to 28,770 in KPN (*K. pneumoniae*), *E. coli*, and *C. koseri* expressing KPC, but was not observed in *E-coli* that did not express KPC.

It could be confirmed that data having sufficiently high resolution were reproducibly obtained even when elution was directly performed on the plate.

Example 4: Identification of KPC Through Pretreatment Using Sonication

Figure 8:
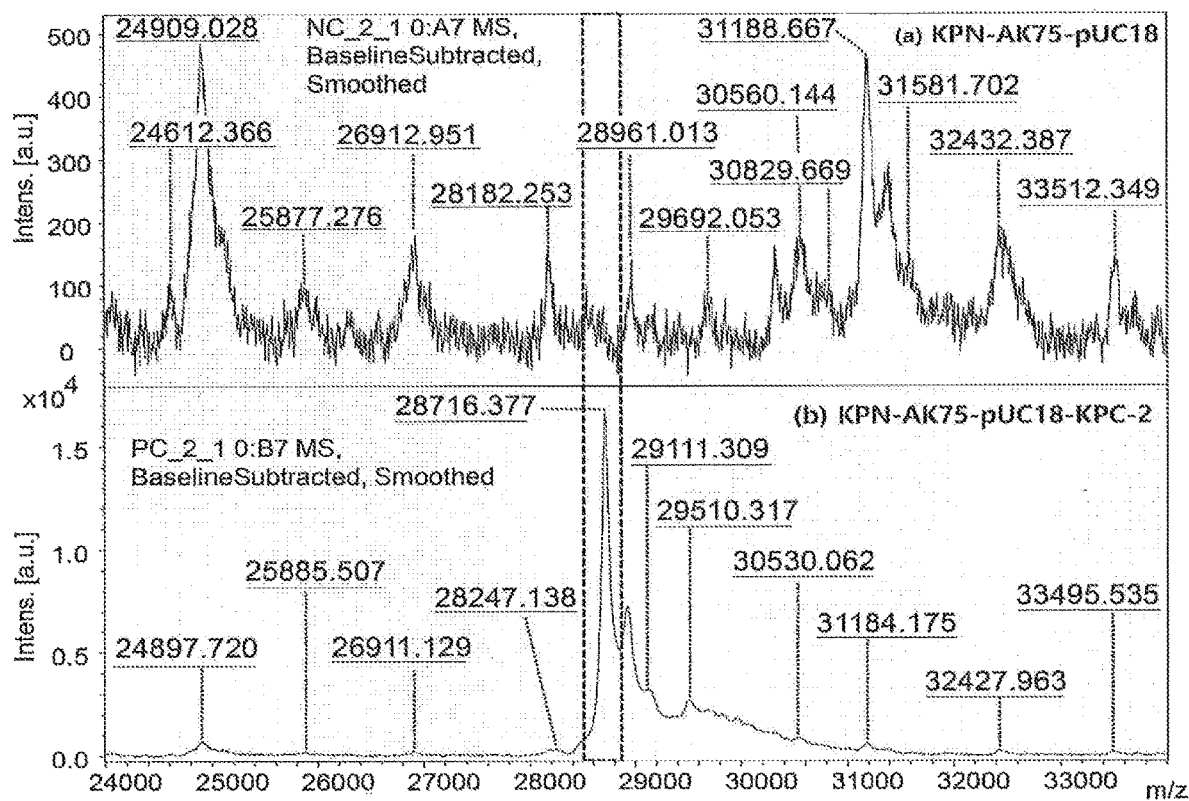
FIG. 8 shows data obtained by identifying the samples that are pretreated using sonication according to an embodiment of the present invention using MALDI-TOF.

The sample obtained through the pretreatment method of 4-2 was identified using MALDI-TOF, and the result is shown in FIG. 8.

Specifically, the bacteria strains cultured in the same manner as in the introduction part of the pretreatment of 4-1 were homogenized in a buffer (this buffer did not contain a detergent). In addition, sonication was performed under 3 seconds on/off and 35 amp condition for 5 minutes. Subsequently, the sample was subjected to centrifugation at 15,000 g for 10 minutes using a centrifuge at room temperature. After the centrifugation, a supernatant was isolated and then identified using MALDI-TOF.

As seen in the results, in the case of FIG. 8*a*, which is a negative control containing only a vector, the peak was not observed at m/z of 28,670 to 28,770, but in the case of FIG. 8*b*, which is a strain expressing KPC-2, a strong peak was confirmed at m/z of 28,670 to 28,770. This is a result value corresponding to the inherent peak of KPC. Therefore, it could be confirmed that even when the *E. coli* strain expressing KPC was pretreated using sonication, data having sufficiently high resolution were reproducibly obtained.

The above Examples are for identifying KPC and/or OXA among carbapenemases. In the cases of genotypes of other decomposing enzymes, that is, GES, SME, IMI, NMC-A, IMP, VIM, SPM, GIM, SIM, NDM, AIM, KHM, and DIM, the enzymes may be identified in an intact state using a mass spectrometer at one time in the same manner.

\*As described above, according to the present invention, it is possible to accurately detect, in a short time CRE and/or CPE, which may cause fatal harm to national health using a simple pretreatment and a popular mass spectrometer. Accordingly, high usefulness is expected to be ensured in the field.

The invention claimed is:

1. A method of directly detecting a beta-lactam antibiotic hydrolase using a mass-spectrometry method, the method comprising the steps of:
    (a). culturing bacterial strains from a biological sample collected from a patient;
    (b). performing pretreatment for mass spectrometry on the cultured bacteria strains obtained from step (a); and
    (c). performing the mass spectrometry on the pretreated material obtained from step (b) using a Matrix-assisted laser desorption ionization-time of flight (MALDI-TOF) mass spectrometer to detect an intact form of the beta-lactam antibiotic hydrolase in the sample,
    wherein the step (b) of performing the pretreatment for the mass spectrometry further comprises lysing the cultured bacterial strains in a lysis buffer that comprises a non-ionic detergent selected from the group consisting of OG (n-octyl-β-D-glucopyranoside), OTG (n-octyl-β-D-thioglucopyranoside), DDM (n-dodecyl-β-D-maltopyranoside), OGNG (octyl glucose neopentyl glycol), and DDTM (n-dodecyl-β-D-thiomaltopyranoside),
    wherein a protease is not used in step (b) of performing pretreatment for the mass spectrometry.

2. The method of claim 1, wherein the lysing is directly performed on a plate for the mass spectrometer.

3. The method of claim 1, wherein the beta-lactam antibiotic hydrolase is an intact form of carbapenemase.

4. The method of claim 3, wherein the carbapenemase has a genotype of KPC, NDM, or OXA.

5. The method of claim 4, wherein, a peak in the range of 28,670 to 28,770 m/z determines the presence of an intact form of KPC.

6. The method of claim 4, wherein, a peak in the range of 28,100 to 28,200 m/z determines the presence of an intact form of OXA.

7. The method of claim 1, wherein the step (b) of performing the pretreatment further comprises:
    homogenizing the cultured bacteria strains in a buffer; and
    sonicating the homogenized culture at room temperature.

8. A kit for directly detecting a beta-lactam antibiotic hydrolase using the mass-spectrometry method as set forth in claim 1, the kit comprising:
    the lysis buffer;
    a matrix for the MALDI-TOF mass spectrometer;
    a first reference material; and
    a second reference material,
    wherein the first reference material comprises the beta-lactam antibiotic hydrolase to be measured, and the second reference material comprises a material for instrument calibration.

9. The kit of claim 8, wherein the beta-lactam antibiotic hydrolase is an intact form of carbapenemase.

10. The kit of claim 9, wherein the carbapenemase has a genotype of KPC, NDM, or OXA.

* * * * *